US012478454B2

(12) United States Patent
Krause et al.

(10) Patent No.: US 12,478,454 B2
(45) Date of Patent: Nov. 25, 2025

(54) LATERAL ACCESS ALIGNMENT GUIDE AND RIGID ARM

(71) Applicant: Stryker European Operations Holdings LLC, Kalamazoo, MI (US)

(72) Inventors: Steven F. Krause, Oakland, NJ (US); Spencer Popejoy, Ringwood, NJ (US); Charles L. Bush, Jr., Wayne, NJ (US); Abram Reitblat, Monroe, NY (US); Douglas G. Pedrick, Newburgh, NY (US)

(73) Assignee: Stryker European Operations Holdings LLC, Portage, MI (US)

( * ) Notice: Subject to any disclaimer, the term of this patent is extended or adjusted under 35 U.S.C. 154(b) by 156 days.

(21) Appl. No.: 18/165,749

(22) Filed: Feb. 7, 2023

(65) Prior Publication Data

US 2023/0255724 A1 Aug. 17, 2023

Related U.S. Application Data

(62) Division of application No. 16/639,410, filed as application No. PCT/US2018/000329 on Aug. 17, 2018, now Pat. No. 11,596,495.

(Continued)

(51) Int. Cl.
*A61B 90/57* (2016.01)
*A61B 17/02* (2006.01)

(Continued)

(52) U.S. Cl.
CPC ............ *A61B 90/57* (2016.02); *A61B 17/025* (2013.01); *A61B 17/8897* (2013.01);

(Continued)

(58) Field of Classification Search
CPC ... A61B 90/50; A61B 90/57; A61B 2090/506; A61B 2090/571; A61G 13/101
See application file for complete search history.

(56) References Cited

U.S. PATENT DOCUMENTS

| | | | | |
|---|---|---|---|---|
| 2,586,488 A | | 2/1952 | Smith | |
| 2,628,803 A | * | 2/1953 | Krewson | A61M 16/06 248/172 |

(Continued)

FOREIGN PATENT DOCUMENTS

| | | | |
|---|---|---|---|
| WO | 2009137700 A1 | 11/2009 | |
| WO | 2018039228 A1 | 3/2018 | |

(Continued)

OTHER PUBLICATIONS

International Search Report for Application No. PCT/US2017/048009 dated Dec. 11, 2017, 7 pages.

(Continued)

*Primary Examiner* — Zade Coley
(74) *Attorney, Agent, or Firm* — Duane Morris LLP

(57) ABSTRACT

In one embodiment, a surgical rigid arm (100, 150, 200, 900) includes a first portion (102, 152, 202, 902), a second portion (103, 153, 203, 903) and a central portion (105, 154, 205, 906), where the central portion is extends between the first and second portions. A first end of the first portion and a second end of the second portion are each attached to a peripheral side (14) of a surgical bed (10, 30) such that the first portion and the second portion extend from the surgical bed in a first direction. The central portion extends substantially horizontally and is positioned over the surgical bed, the central portion being connected to the surgical instrument such that a load from the surgical instrument is (Continued)

distributed across the central portion to the first portion and second portion to provide rigid support for the surgical instrument.

8 Claims, 20 Drawing Sheets

Related U.S. Application Data

(60) Provisional application No. 62/546,780, filed on Aug. 17, 2017.

(51) Int. Cl.
*A61B 17/88* (2006.01)
*A61B 90/50* (2016.01)
*A61G 13/00* (2006.01)
*A61G 13/10* (2006.01)

(52) U.S. Cl.
CPC .......... *A61B 90/50* (2016.02); *A61G 13/0054* (2016.11); *A61G 13/101* (2013.01); *A61B 2017/0256* (2013.01); *A61B 2090/506* (2016.02); *A61B 2090/571* (2016.02)

(56) References Cited

U.S. PATENT DOCUMENTS 3,221,743 A 12/1965 Thompson et al.
3,394,700 A 7/1968 Yamamoto
3,859,993 A * 1/1975 Bitner ................. A61M 16/009 5/507.1
4,617,916 A * 10/1986 LeVahn .................. A61B 90/50 600/231
4,718,151 A 1/1988 LeVahn et al.
4,726,356 A * 2/1988 Santilli .............. A61B 17/0206 600/234
4,813,401 A * 3/1989 Grieshaber ............ A61B 17/02 600/234
4,865,019 A 9/1989 Phillips
4,949,707 A 8/1990 LeVahn et al.
4,971,037 A 11/1990 Pelta
4,971,038 A 11/1990 Farley
5,888,197 A 3/1999 Mulac et al.
5,897,087 A * 4/1999 Farley .................... A61B 90/50 248/316.2
6,179,262 B1 * 1/2001 Ellard ................ F16M 11/2078 248/278.1
6,234,961 B1 5/2001 Gray
6,258,089 B1 7/2001 Campbell et al.
6,511,423 B2 1/2003 Farley
6,602,190 B2 * 8/2003 Dobrovolny ....... A61B 17/0206 600/234
7,458,933 B2 12/2008 LeVahn et al.
8,231,528 B1 * 7/2012 Friedrich .................. B25B 5/16 600/231
8,343,065 B2 1/2013 Bartol et al.
8,343,079 B2 1/2013 Bartol et al.
8,517,954 B2 8/2013 Bartol et al.
8,545,531 B2 10/2013 Geist et al.
8,635,725 B2 1/2014 Tannoury et al.
8,852,090 B2 * 10/2014 Friedrich ............... A61B 17/02 600/231
8,855,822 B2 10/2014 Bartol et al.
8,882,679 B2 11/2014 Bartol et al.
8,892,259 B2 11/2014 Bartol et al.
8,932,215 B2 * 1/2015 Friedrich .................. B25B 5/16 600/230
8,942,797 B2 1/2015 Bartol et al.
8,979,767 B2 3/2015 Bartol et al.
8,983,593 B2 3/2015 Bartol et al.
8,992,558 B2 3/2015 Stone et al.
9,039,630 B2 5/2015 Bartol et al.
9,084,550 B1 7/2015 Bartol et al.
9,301,711 B2 4/2016 Bartol et al.
9,320,506 B2 4/2016 Bertagnoli et al.
9,433,551 B2 * 9/2016 Allen ..................... A61B 50/33
9,458,935 B2 10/2016 Fricke et al.
9,615,987 B2 4/2017 Worm et al.
2002/0133174 A1 * 9/2002 Charles .................. A61B 34/70 606/130
2002/0161446 A1 * 10/2002 Bryan ................ A61B 17/1671 623/17.15
2003/0229273 A1 * 12/2003 Mulac .................... A61B 90/50 600/234
2005/0119531 A1 6/2005 Sharratt
2006/0135852 A1 6/2006 Koros et al.
2006/0206009 A1 9/2006 Von Wald et al.
2007/0213591 A1 9/2007 Aizenfeld et al.
2008/0214925 A1 * 9/2008 Wilson ................... A61B 5/055 600/410
2010/0178100 A1 7/2010 Fricke et al.
2010/0241129 A1 9/2010 Markey et al.
2012/0232349 A1 9/2012 Perrow
2012/0265021 A1 * 10/2012 Nottmeier ................ A61B 1/32 606/279
2014/0107707 A1 * 4/2014 Rovner .............. A61B 17/7002 606/279
2014/0114135 A1 4/2014 Ellman
2015/0018623 A1 1/2015 Friedrich et al.
2015/0018625 A1 1/2015 Miraki et al.
2015/0051506 A1 2/2015 Wybo et al.
2015/0051507 A1 2/2015 Wybo et al.
2015/0088029 A1 3/2015 Wybo
2015/0250672 A1 * 9/2015 Fossez ................. A61G 13/125 5/630
2015/0257958 A1 * 9/2015 Allen ................... A61G 13/101 108/49
2016/0051241 A1 2/2016 Vogtherr et al.
2016/0183913 A1 6/2016 Singh et al.
2016/0242736 A1 8/2016 Freiburg et al.
2016/0345949 A1 12/2016 Harvey et al.
2017/0014118 A1 1/2017 Capote
2017/0014119 A1 * 1/2017 Capote ................... A61B 90/50
2017/0065268 A1 3/2017 Sindram
2019/0053826 A1 2/2019 Bush, Jr. et al.

FOREIGN PATENT DOCUMENTS

WO 2019036036 A1 2/2019
WO 2019036048 A2 2/2019

OTHER PUBLICATIONS

Bush et al., U.S. Appl. No. 62/546,841, filed Aug. 17, 2017, titled “Independent Rod Suspension”.
Popejoy et al., U.S. Appl. No. 62/546,796, filed Aug. 17, 2017, titled “Bridges and Lighting for Lateral Access”.
International Search Report and Written Opinion for PCT/US2018/000329, mailed Jan. 3, 2019.

* cited by examiner

LATERAL ACCESS ALIGNMENT GUIDE AND RIGID ARM

CROSS-REFERENCE TO RELATED APPLICATIONS

The present application is a divisional of U.S. patent application Ser. No. 16/639,410, filed Feb. 14, 2020, which is a national phase entry under 35 U.S.C. § 371 of International Application No. PCT/US2018/000329 filed on Aug. 17, 2018, which claims the benefit of the filing date of U.S. Provisional Application No. 62/546,780, filed on Aug. 17, 2017, the disclosures of which are hereby incorporated by reference herein in their entirety. Additionally, the disclosure of commonly owned WO2018/039228, filed Aug. 22, 2017 ("the '228 Publication"), and commonly owned U.S. Provisional Patent Application Nos. 62/546,847 ("the '847 Application), 62/546,841 ("the '841 Application"), 62/546,796 ("the '796 Application") and 62/650,579 ("the '579 Application"), are also hereby incorporated by reference herein in their entirety.

BACKGROUND OF THE INVENTION

Spinal implants are commonly utilized in spinal procedures designed to treat spinal maladies. Such implants are used, for example, to immobilize and fuse adjacent vertebral bodies. This often plays a critical role in addressing spinal diseases or injury, or otherwise treating pain in a patient.

Various techniques have been developed and are often employed to access the spine during a spinal implant implantation procedure. These techniques are often dictated by the type of implant being utilized. For example, the spine may be accessed using a posterior approach, an anterior approach, or a lateral approach. Among these, a lateral approach is advantageous in that a portal to access a surgical site may be larger than with other approaches, thus allowing for a larger implant to be used, which experience over time has shown tends to improve the overall outcome of the procedure.

One method for implanting lateral implants is via a lateral trans-psoas approach. This typically involves the creation of an incision on the lateral side of the patient. Thereafter, a path to a surgical site, i.e., the vertebral bodies, is systematically created. One technique to accomplish this involves the use of sequential dilators, where an insertion of each dilator over another progressively increases the size of a tissue area displaced by the dilators. Once the dilators have displaced a sufficient amount of tissue for the procedure, a retractor, ring or other stabilizing structure is used to preserve an opening. Retractors typically include a plurality of blades that are designed to rest against the vertebral bodies and hold the tissue open to allow access for the surgeon. In a variant, a narrow retractor employing blades in the form of rods are initially inserted and sequential dilation is used to move the rods apart and create the path to the surgical site.

Retractor systems are generally attached to surgical clamps which are in turn attached to the surgical bed. Surgical clamps often include multiple arms, connectors and adjustment mechanisms that are attached away from the surgical site to prevent these components from restricting access to a target surgical site. Consequently, clamps with long extended arms anchored away from the surgical site are used to connect the retractor system. These clamps are therefore susceptible to the "springboard effect," which prevents rigid positioning to hold the retractor system in a fixed position. The springboard effect is further exacerbated during the course of a surgery because the retractor assembly is subject to considerable static and impact loads.

Another drawback of existing devices for such spinal surgery is the excessive use of X-ray imaging or other visualization techniques during and after positioning of the retractor system. X-ray equipment need considerable space and clearances to be positioned in multiple locations during the course of the surgery. This often requires considerable time and effort to move the x-ray equipment around the surgical bed. Further, the retractor assembly must generally be vertical to the target surgical site for lateral spinal surgery. However, aligning the retractor assembly using x-ray imaging is challenging within the restricted operating space and typically requires considerable time and effort.

Therefore, there exists a need for improved surgical instruments for spinal surgery, in particular, lateral access spinal surgery.

BRIEF SUMMARY OF THE INVENTION

Disclosed herein are surgical rigid arms for supporting surgical instruments and surgical alignments guides.

In a first aspect of the present disclosure, a surgical rigid arm for supporting surgical instrument is provided. The surgical rigid arm may have a first portion with a first end, a second portion with a second end, and a central portion disposed between the first and second portions. The first and second ends may be attached to a peripheral side of a surgical bed such that the first portion and second portion may extend from the surgical bed in a first direction. The central portion may extend substantially horizontally to the first and second portions and may be positioned above an interior of the surgical bed. The central portion may be connected to the surgical instrument such that a load from the surgical instrument may be distributed across the central portion to the first portion and second portion to provide rigid support for the surgical instrument.

In accordance with the first aspect, the central portion may include a platform extending into the interior of the surgical bed and the surgical instrument may be connected to the platform. The platform may be moveably connected to the central portion. The platform may be moveable with respect to the central portion by a linear actuator.

In accordance with the first aspect, a distance between the first end and the second end may be less than a length of the peripheral side of the surgical bed. A distance between the first end and the second end may be greater than a distance between the central portion and the peripheral side of the surgical bed. The first end and second end may be attached to a bed rail of the surgical bed. The first end and second end may be attached to the bed rail by first and second sliding clamps respectively. The first and second sliding clamps may be slidably engaged with the bed rail in an unlocked position such that the rigid arm may be positioned along the bed rail and secured by locking the sliding clamps. The bed rail may be located on a long side of the surgical bed.

Further in accordance with the first aspect, the first and second portions may include telescopic segments to vertically move central portion with respect to the surgical bed. The central portion may include a telescopic segment to horizontally move the central portion with respect to the first and second portions.

In a second aspect of the present disclosure, a surgical rigid arm for supporting surgical instrument is provided. The surgical rigid arm may have a first portion with a first end, a second portion with a second end, and a central portion disposed between the first and second portions. The first portion may be attached to a first peripheral side of a surgical bed and may extend from the surgical bed in a first direction. The second end may be attached to a second peripheral side of the surgical bed and may extend from the surgical bed in the first direction. The central portion may be substantially horizontal to the first and second portions and may be positioned above an interior of the surgical bed. The central portion may be detachably connected to a surgical instrument such that a load from the surgical instrument may be distributed across the central portion to the first portion and the second portion to provide rigid support for the surgical instrument.

In a third aspect of the present disclosure, a positional adjuster for a surgical instrument is provided. The positional adjuster may include an adjustable first linear actuator, an adjustable second linear actuator, an adjustable third linear actuator, an adjustable bearing joint, a first and a second section. The adjustable first linear actuator may position a surgical instrument in a proximal-distal direction. The adjustable second linear actuator may position the surgical instrument in an anterior-posterior direction. The adjustable third linear actuator may position the surgical instrument in a medial-lateral direction. The adjustable bearing joint may allow rotation of the surgical instrument in at least a first and a second plane. The first section may be detachably attached to a body. The second section may be detachably attached to the surgical instrument.

In accordance with this third aspect, the first, second and third linear actuators may be any of a mechanical, electromechanical and hydraulic actuator. The first, second and third linear actuators may be rack and pinion actuators. The positional adjuster may include a biasing member to bias the surgical instrument towards the surgical bed. The biasing member may be spring loaded. The adjustable bearing joint may be a spherical bearing joint. The adjustable bearing joint may be a gimbal.

Further in accordance with this third aspect, the positional adjuster may include a second adjustable bearing joint to allow rotation of the surgical instrument in at least a third plane. The first, second and third linear adjusters and the bearing joint may include locking means such that the surgical instrument can be locked in a fixed position. The surgical instrument may be retractor. The body may be a rigid arm.

In a fourth aspect of the present disclosure, a frame for securing a surgical instrument is provided. The frame may have a harness mountable on a lateral body region of a patient positioned on a surgical bed and at least one attachment member to secure the harness to a first side of the surgical bed such that the harness may contact the lateral body region to constrain the patient on the surgical bed. The harness may be contoured to correspond to the lateral body region such that the harness may extend in an anterior to a posterior direction when mounted on the lateral body region. The harness may have a central window for access to the lateral body region and for attachment to a surgical instrument.

In accordance with this fourth aspect, the surgical instrument may a spinal lateral retractor. The frame may include a second attachment member attached to a second side of the harness and a second side of the surgical bed. The frame may include third and fourth attachment members attached to the harness and may be positioned parallel to the first and second attachment members. The harness may be moveable in a track formed by the first and second member on a first side of the harness and the third and fourth member on a second side of the harness.

In a fifth aspect of the present disclosure, a frame for securing a surgical instrument is provided. The frame may include a rectangular window to access a lateral body region of a patient positioned on a surgical bed, and at least one attachment member to secure the frame to a rigid member such that the frame may be biased on the lateral body region to constrain the patient on the surgical bed. The rectangular window may be placed over the lateral body region such that at least a portion of the frame may contact the lateral body region. One or more legs may extend from one or more corners of the rectangular window. Each leg may contact the surgical table. The central window may be attached to a surgical instrument. The surgical instrument may be a spinal lateral retractor. The surgical bed may have a concave surface corresponding to the patient's body such that the surgical bed may further secure the patient with the frame.

In a sixth aspect of the present disclosure, a rigid arm for supporting a surgical instrument is provided. The rigid arm may include a first portion having a first end, a second portion having a second end and a central portion disposed between the first and second portions. The first and second ends may be attached to a first and second strap on a surgical bed such that the first portion and second portion may extend from the surgical bed in a first direction. The central portion may extend substantially horizontally to the first and second portions and may extend towards an interior of the surgical bed. The central portion may be connected to the surgical instrument such that a load from the surgical instrument may be distributed across the central portion to the first portion and second portion to provide rigid support for the surgical instrument.

In a seventh aspect of the present disclosure, a surgical kit for performing lateral access spinal surgery with a retractor is provided. The surgical kit may include a rigid arm and a positional adjuster. The rigid arm may include a first portion having a first end, a second portion having a second end, and a central portion disposed between the first and second portions. The first and second ends may be attached to a peripheral side of a surgical bed such that the first portion and second portion may extend from the surgical bed in a first direction. The central portion may be substantially horizontal to the first and second portions and positioned above an interior of the surgical bed.

The positional adjuster may include an adjustable first linear actuator, an adjustable second linear actuator, an adjustable third linear actuator, an adjustable bearing joint, a first and a second section. The adjustable first linear actuator may position the retractor in a proximal-distal direction. The adjustable second linear actuator may position the retractor in an anterior-posterior direction. The adjustable third linear actuator may position the retractor in a medial-lateral direction. The adjustable bearing joint may allow rotation of the retractor in at least a first and a second plane. The first section may be detachably attached to the central portion of the rigid arm. The second section may be detachably attached to the retractor. The central portion may be connected to the positional adjuster such that a load from the retractor may be distributed across the central portion to the first portion and the second portion to provide rigid support for the retractor.

In an eight aspect of the present disclosure, an alignment guide for a lateral access spinal surgery is provided. The alignment guide may be coupled with a retractor. The alignment guide may include a first frame having first and second elements, a second frame having third and fourth elements, and a linking element connecting the first frame to the second frame such that the first frame and second frame may be parallel to each other. The first and second elements may intersect at a first intersection. The first and second element may span across the first frame. The second and third elements may intersect at a second intersection. The second frame may be identical to the first frame. When the alignment guide is viewed along a first line, the first and second elements may be aligned with the second and third elements and the first line connecting the first and second intersections.

In accordance with this aspect, the first and second intersections may be at the center of the first and second frames respectively. The first and second intersections may form first and second circular openings respectively, such that a guidewire may be inserted through the first and second circular openings. Each of the first and second frames may include one or more detachable segments, such that a guidewire inserted through the first and second circular openings may be removed laterally from the alignment guide by detaching one of the detachable segments from each of the first and second frames. The alignment guide may include a level to indicate if the first frame is horizontally or vertically positioned.

A ninth aspect of the present disclosure is a method for aligning a surgical retractor for lateral access spinal surgery with an alignment guide. A method in accordance with this aspect of the disclosure may include the steps of positioning an alignment guide over a target surgical site, aligning the alignment guide such that a first and a second frame are parallel to a target site, inserting a guidewire through a first and a second circular opening to contact the target surgical site, removing the alignment guide while retaining a vertically positioned guidewire, attaching a surgical retractor with reference to the positioned guidewire, and aligning the surgical retractor with the positioned guidewire to vertically align the surgical retractor over the target surgical site. The alignment guide may include the first frame, the second frame and a linking element connecting the first frame to the second frame. The first frame may have first and second elements. The first and second elements may intersect at a first intersection. Each element may span across the first frame. The second frame may have a third and a fourth elements. The second and third elements may intersect at a second intersection. The second frame may be identical to the first frame. The linking element may connect the first frame to the second frame such that the first frame and second frame may be parallel to each other. The first and second intersections may form the first and second circular openings respectively, such that the guidewire may be inserted through the first and second circular openings. When the alignment guide is viewed along a first line, the first and second elements may be aligned with the second and third elements, and the first line connecting the first and second intersections.

BRIEF DESCRIPTION OF THE DRAWINGS

A more complete appreciation of the subject matter of the present disclosure and the various advantages thereof can be realized by reference to the following detailed description, in which reference is made to the following accompanying drawings.

DETAILED DESCRIPTION

Reference will now be made in detail to the preferred embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term “a,” as used in the specification, means “at least one.” The terminology includes the words above specifically mentioned, derivatives thereof, and words of similar import.

In describing preferred embodiments of the disclosure, reference will be made to directional nomenclature used in describing the human body. It is noted that this nomenclature is used only for convenience and that it is not intended to be limiting with respect to the scope of the disclosure. For example, as used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Figure 1:
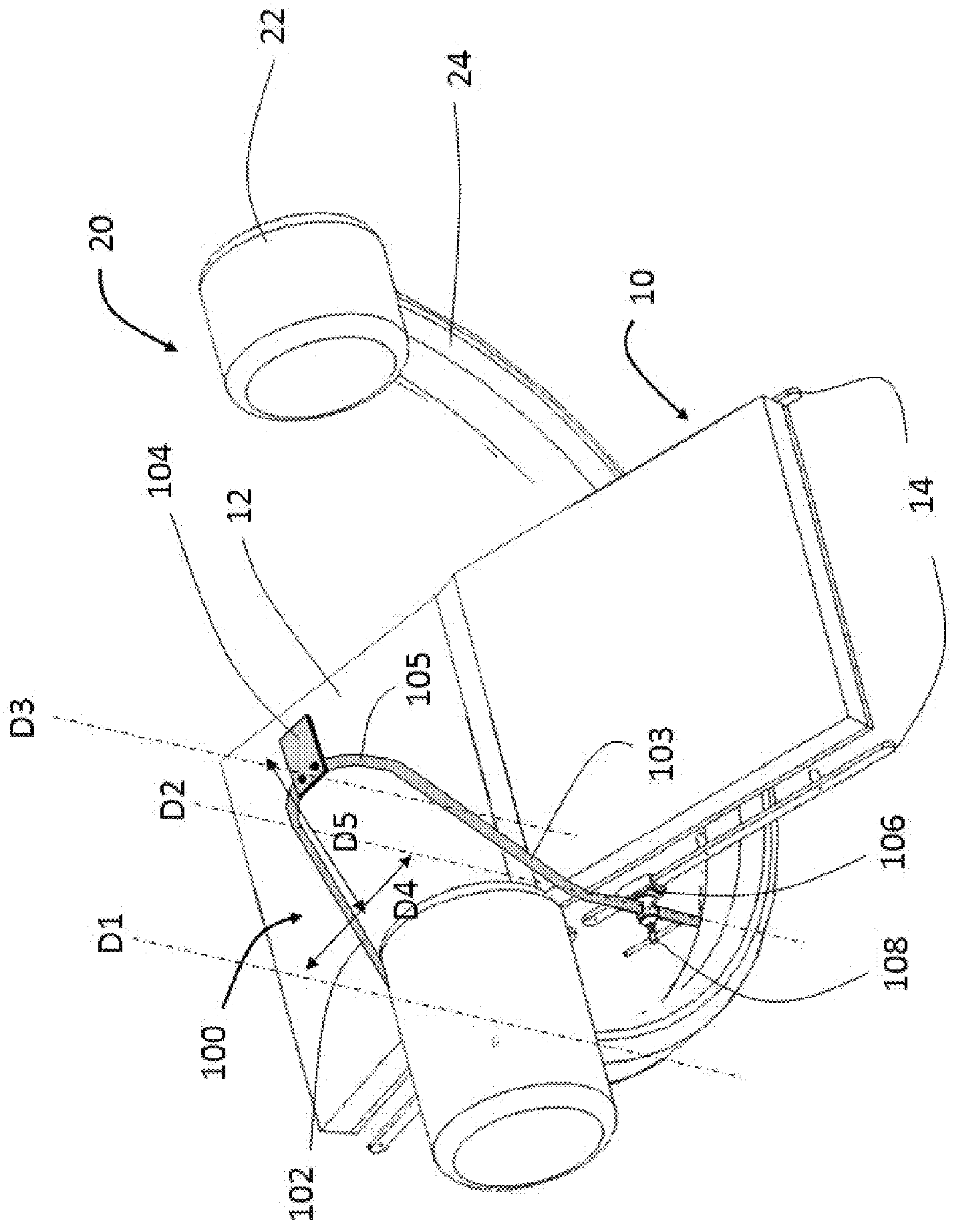
FIG. 1 is a perspective view of a rigid arm attached to a surgical bed according to one embodiment of the present disclosure.

FIG. 1 shows a perspective view of a rigid arm 100 according to one embodiment of the present disclosure attached to a surgical bed 10. Rigid arm 100 includes a first arm 102, a second arm 103 and a central arm 105. Arms 102 and 103 are attached to bed rails 14 by a slide assembly 106 allowing arms 102 and 103 to be positioned at different locations along bed rail 14. Arms 102 and 103 extend vertically above bed rails 14 along axis D1 and D2 respectively until the arms have cleared the edge of the surgical bed 10, at which point the arms 102 and 103 are bent such that they continue to extend vertically, but also horizontally over bed surface 12. Central arm 105 is generally horizontal to bed rails 14 and located over interior bed surface 12 as indicated by axis D3. A utility plate 104 is located on central arm 104 as best shown in FIG. 1. As more fully described below, surgical instruments may be connected to utility plate 104. It is to be understood that the specific manner in which arms 102, 103, and 105 extend can vary in other embodiments according to the present disclosure. The specific shapes and sizes of such components can vary as well.

Arms 102 and 103 are secured to one side of surgical table 10 through slide assembly 106 and a set screw 108 which interface with one set of bed rails 14. Where the arms interface with slide assembly 106, the arms are capable of vertical movement along axes D1 and D2 in order to broadly position the arms vertically relative to the bed surface 12. Additionally, slide assemblies 106 are capable of sliding along bed rails 14 in order to position rigid arm 100 at different positions along the length of the surgical bed 10. When utility plate 104 has reached its desired location relative to the surgical table 10, set screw 108 secures the arms 102 within slide assembly 106 against bed rails 14. Slide assembly 106 can also pivot with respect to bed rails 14. For example, when surgical bed 10 is inclined along a central axis as shown in FIG. 1 to properly position a patient, slide assembly 106 can be rotated about bed rail 14 such that axes D1 and D2 are generally transverse to the surgical site. It is to be understood that various components can be utilized to attach rigid arm 100 to a bed, including, but not limited to, various existing bed rail clamps. For instance, it is contemplated to utilize bed rail clamps similar to those disclosed in U.S. Pat. No. 9,615,987 and U.S. Patent Application Publication No. 2015/0250672, the disclosures of which are hereby incorporated by reference herein as it is fully set forth herein.

Surgical equipment load or any other load applied to central arm 105 or to the attached utility plate 104 will be distributed to both arms 102 and 103. A distance D4 defined by first arm 102 and second arm 103 represents a base of rigid arm 100. A second distance D5 defined by axis D3 and bed rail 14 represents the horizontal projection of central arm 105 over surgical bed 10. Distance D4 is preferably greater than D5 to ensure that the base of rigid arm 100 is greater than its horizontal project to maximize rigidity of the rigid arm to allow for surgical procedures where considerable force is applied to the surgical instrument. For example, a surgeon can use the rigid arm to attach a lateral retractor and proceed to use a slap hammer to remove surgical instruments without risking displacement of the lateral retractor. The stability provided by rigid arm 100 will absorb the impact load of the slap hammer without displacing the lateral retractor. Any "springboard effect," wherein the surgical instrument is displaced, often vertically, on account of being suspended by a single, horizontally extending arm is mitigated or eliminated by distributing the load to two arms of rigid arm 100 and by having a base that is larger than the horizontal projection to create a stable construct that is not prone to displacement.

The space defined by distances D4 and D5 will provide sufficient clearance for readily locating an x-ray system 20 between rigid arm 100 to obtain x-ray images anywhere along surgical bed 10. Furthermore, all component of rigid arm 100 are located on one side of surgical bed 10 and therefore provide unrestricted access to a surgeon located on an opposite or transverse side of the surgical bed. Rigid arm 100 may also be adjusted to permit a surgeon to perform a surgical procedure by being positioned between the first and second arm. The horizontal projection of rigid arm 100, defined by distance D5, will allow a surgeon to stand or sit between the rigid arms and access a target surgical site.

Figure 2:
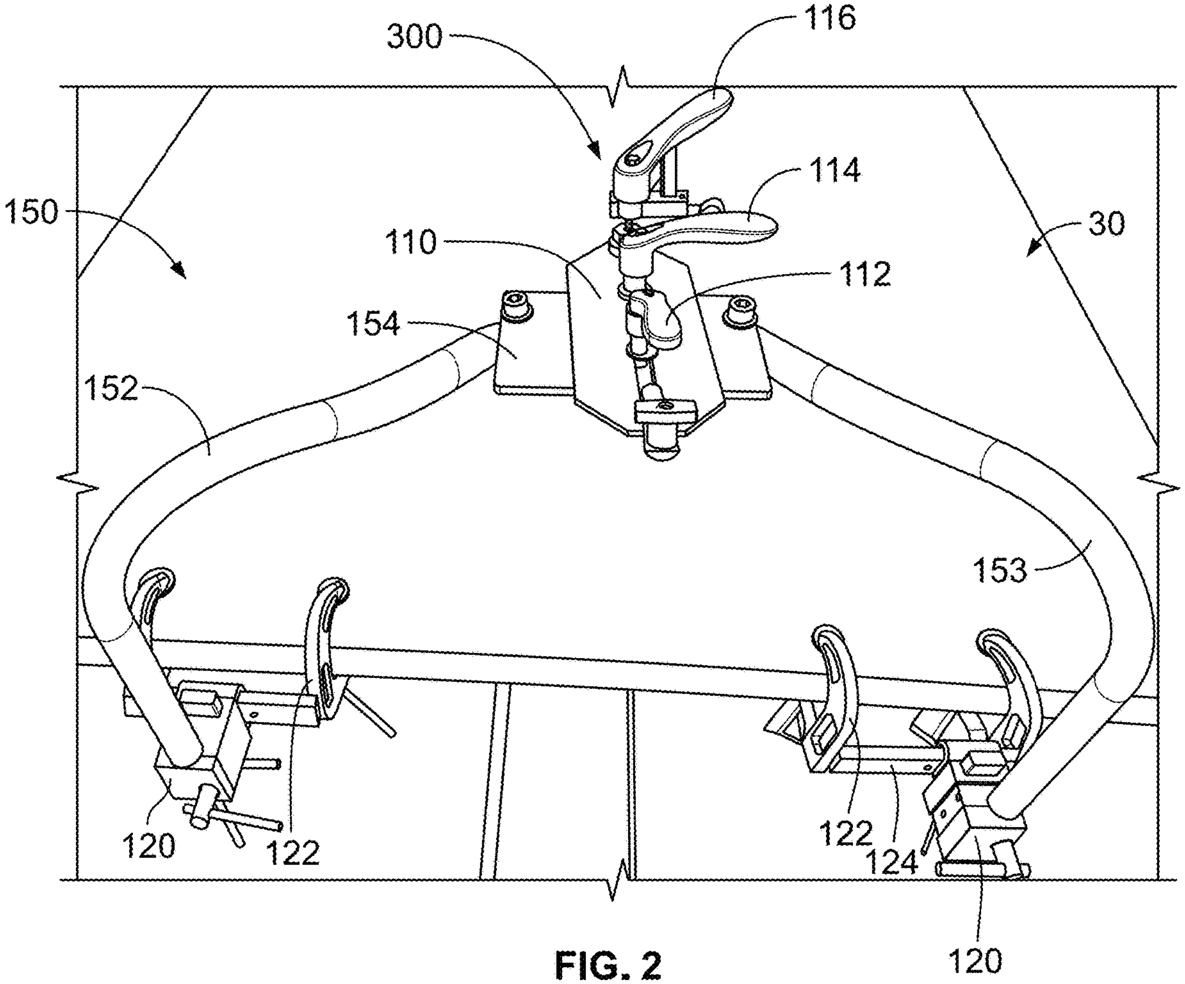
FIG. 2 is a perspective view of a rigid arm attached to a surgical bed according to another embodiment of the present disclosure.

FIG. 2 shows a rigid arm 150 attached to a surgical bed 30 according to another embodiment of the present disclosure. Rigid arm 150 is generally similar to rigid arm 100 but is attached directly to a short-side of surgical bed 30 by attaching a first arm 152 and a second arm 153 with a clamping assembly 122. Clamping assembly includes a clamp rail 124 and a sliding block 120 to adjustably position rigid arm on surgical bed 30. These components are preferably utilized when bed rail attachment is not possible or preferred. Also shown in FIG. 2, is an adjustment platform 110 attached to utility plate 104. Adjustment platform 110 is attached to a positional adjuster 300, which can be connected to a surgical equipment (not shown) to allow for precise positioning of the surgical equipment. This is more fully described below.

Figure 3A:
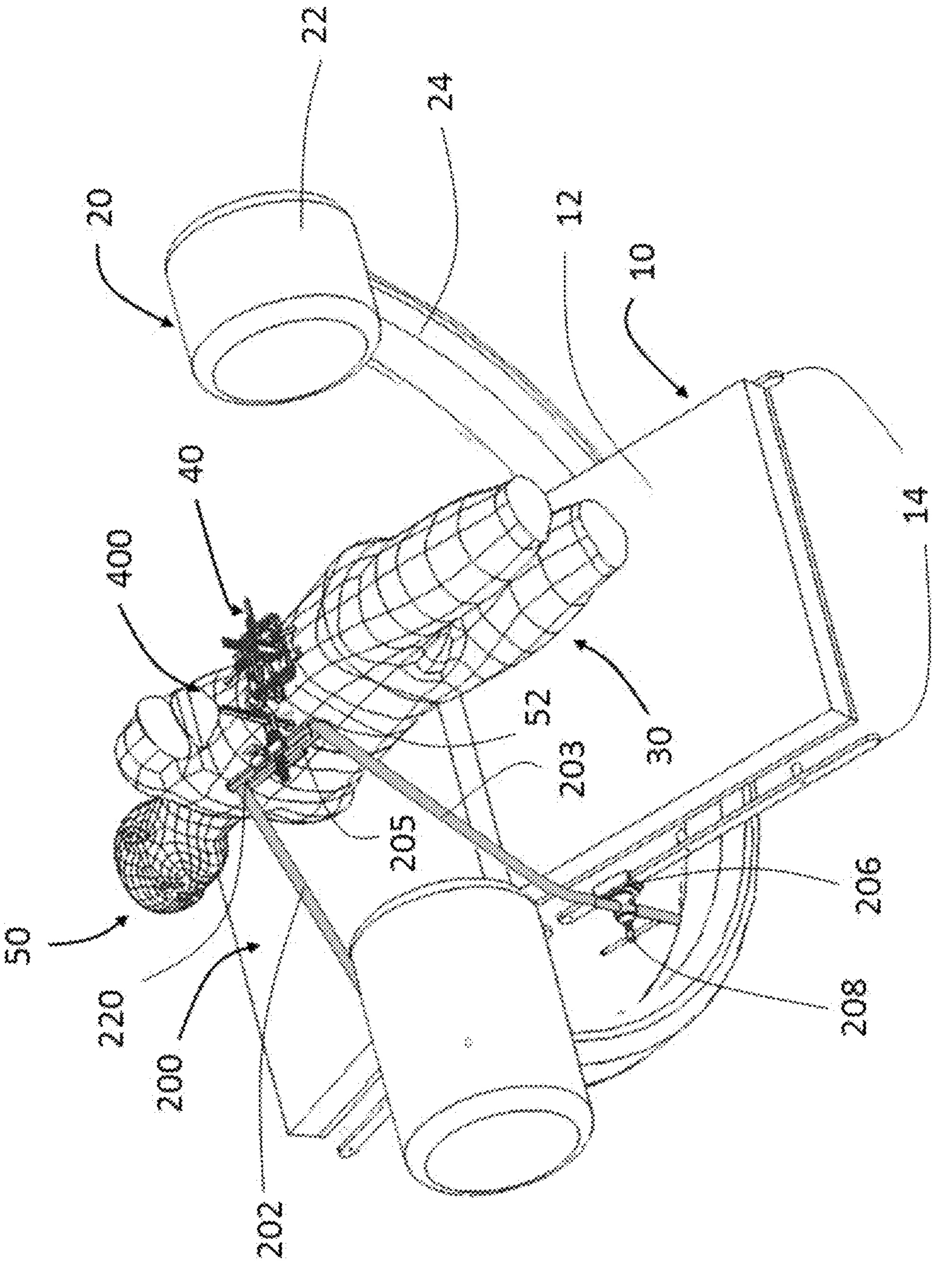
FIG. 3A is a perspective view a rigid arm attached to a surgical bed according to yet another embodiment of the present disclosure.

Referring now to FIG. 3A, there is shown a rigid arm 200 according to a second embodiment of the present disclosure attached to surgical bed 10. Rigid arm 200 is similar to rigid arm 100, and therefore like elements are referred to with similar numerals within the 200-series of numbers. For instance, rigid arm 200 includes first arm 202 and second arm 203 attached to bed rail 14. However, a central arm 205 in this embodiment includes an adjustment plate 220. Adjustment plate 220 is attached to a positional adjuster 400, which is connected to lateral retractor assembly 40 to allow for precise positioning of the lateral retractor as more fully described below. Also shown in FIG. 3A, is a patient 50 positioned on surgical bed 30 for a lateral surgical procedure, whereby the lateral retractor assembly 40 is positioned over the target surgical location 52. All components of rigid arm 100 are located on one side of surgical bed 10 and therefore provide unrestricted access to a surgeon located on an opposite or transverse side of the surgical bed.

Figure 3B:
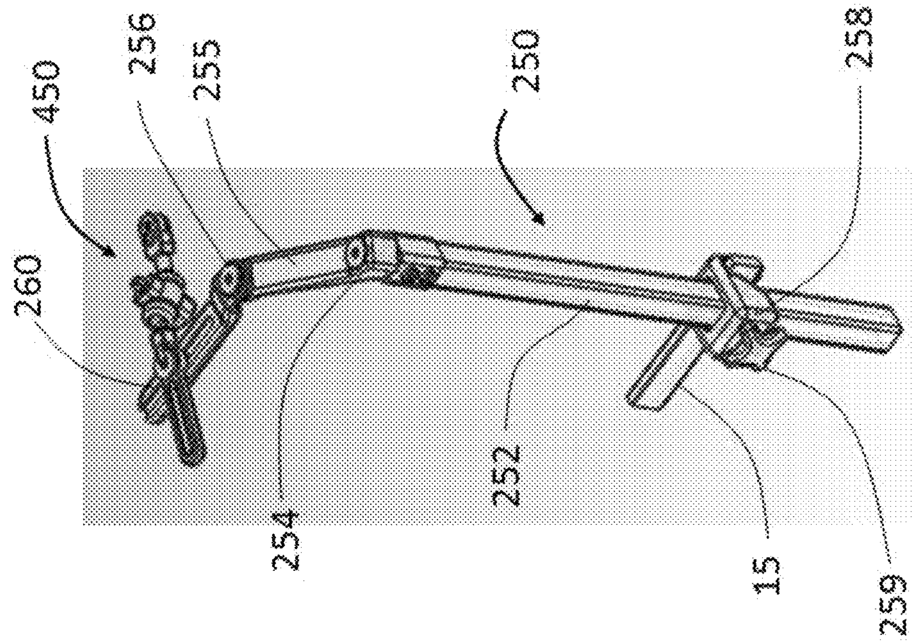
FIG. 3B is a perspective view of a rigid arm attached to a surgical bed according to yet another embodiment of the present disclosure.
Figure 3C:
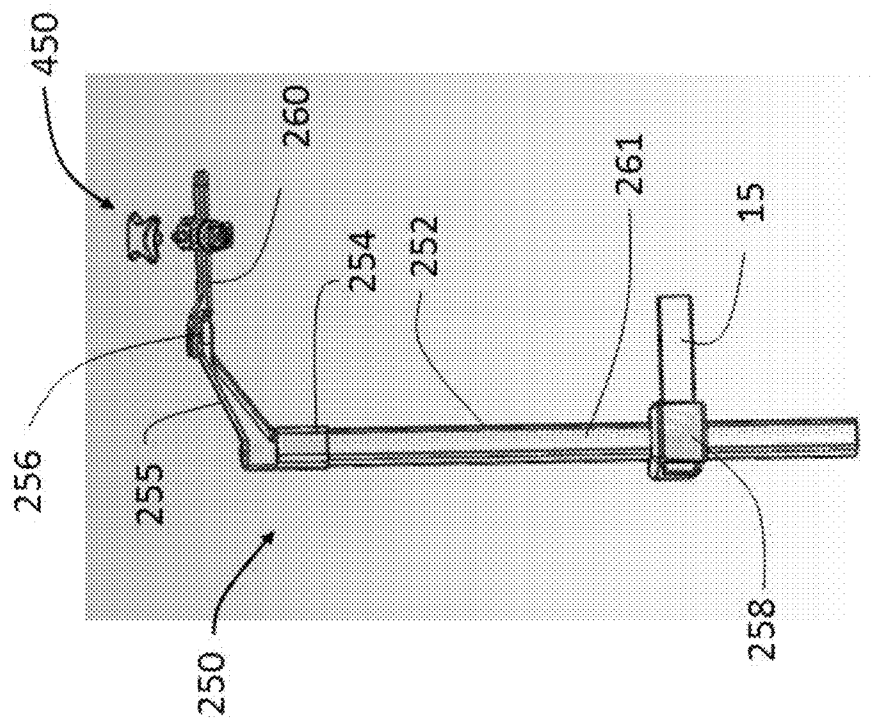
FIG. 3C is a side view of the rigid arm of FIG. 3B.

FIGS. 3B and 3C show perspective and side views of a rigid arm 250 according to another embodiment of the present disclosure. Rigid arm 250 incudes a first arm 252 attached directly to a surgical bed frame component 15. Attaching directly to the bed frame allows rigid arm 250 to be rigidly secured on surgical beds which may have side rails that have sprung loose and consequently fail to provide secure rail attachment points. Alternatively, first arm 252 may be attached to bed rail 14 (not shown) as described in rigid arms 100 or 200. A sliding assembly 258 with a set screw 259 allows first arm 252 to be vertically and horizontally moved and positioned with respect bed frame component 15. First arm 252 has a rectangular cross-section having a thick wall with an inner layer 261. This rigid construction allows rigid arm 250 to withstand static and impact loads during a surgical procedure. Alternative embodiments of rigid arm 250 may include circular or other cross-sections with double-walled or triple-walled constructions having shock-absorbing layers to provide further rigidity. A second arm 255 is attached to first arm 252 by a first rotation joint 254 which allows second arm to rotate about first arm 252. An opposite end of the second arm is secured to an adjustment plate 260 by a second rotation joint 256 as best shown in FIG. 3C. Adjustment plate 260 can be positioned by rotating one or both rotation joints. A positional adjuster 450 attached to adjustment plate 260 can be connected to a lateral retractor assembly or any other surgical instrument. As shown herein, rigid arm 250 requires only a single-point connection to the surgical bed and has only a single arm, i.e., first arm 252, extending over the surgical site and consequently provides improved accessibility to the surgical site.

Rigid arms 100 and 200 may be monolithic or include separate arms which may be assembled. For instance, arms 102, 103 and 202, 203 may include telescopic elements to adjust the height of the rigid arm. Central arm may also include length adjusting elements to adjust the distance between arms 102, 103 and 202, 203 and thereby control the ratio between the base and horizontal projection of the rigid arm for adjusting the stability of the rigid arm. While rigid arms connected to one side of a surgical bed are shown herein, other embodiments may include a rigid arm attached to two different sides of a surgical bed. For example the first arm may be attached to a long side (i.e., along the longitudinal length of the bed) of the surgical bed and the second arm may be attached to a short side (i.e., the "head" or "foot" of the bed) of the surgical bed.

Figure 4:
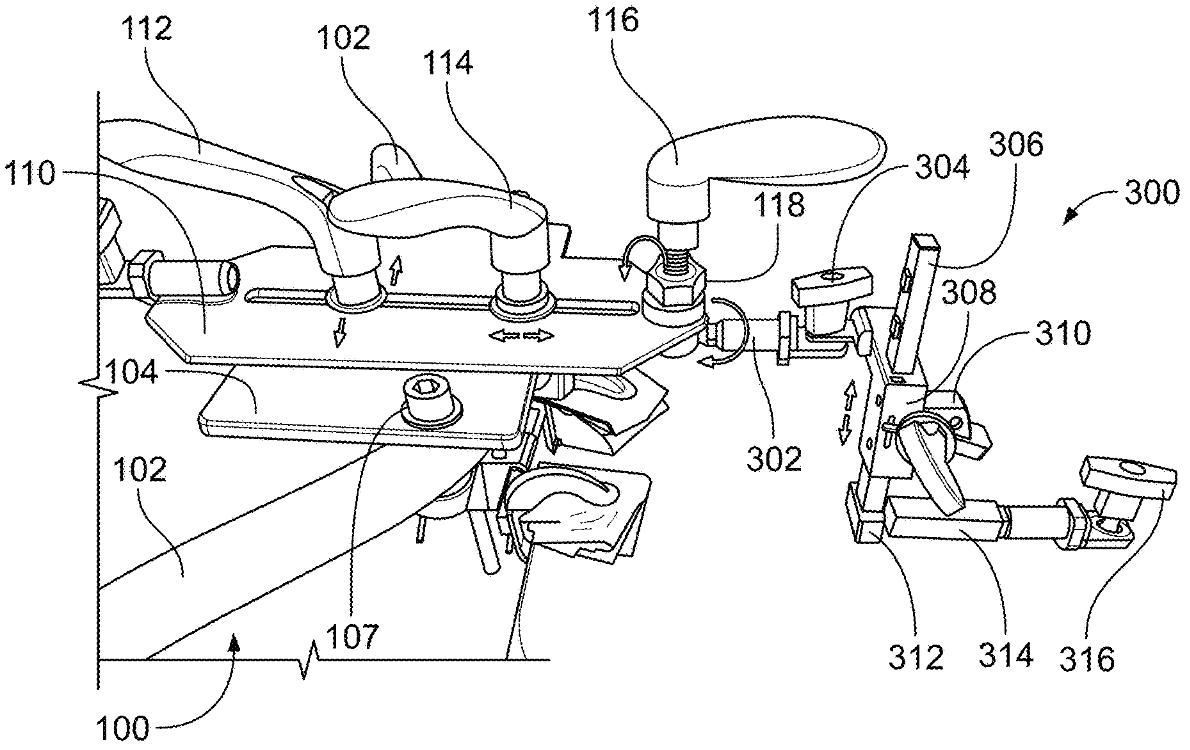
FIG. 4 is a perspective view of a positional adjuster attached to the rigid arm of FIG. 1 according to one embodiment of the present disclosure.

FIG. 4 shows adjustment platform 110 and a positional adjuster 300 attached thereto according to one embodiment of the present disclosure. Adjustment platform 110 is attached to central arm 105 of rigid arm 100 by a pair of screws 107. Adjustment platform 110 has a first handle 112, a second handle 114 and a third handle 116. First handle 112 and second handle 114 allow positional adjustment of adjustment platform 110 in a superior-inferior and medial-lateral direction, respectively. Third handle 116 allows angular adjustment of positional adjuster 300. All three handles can be moved from an unlocked mode for making adjustments to a locked mode to secure the surgical instrument (not shown) to the desired position.

Positional adjuster 300 is attached to adjustment platform 110 by a spherical joint 118. Positional adjuster 300 can be angularly rotated in two planes by moving handle 116 to an unlocked mode. A linking rod 302 extending from spherical joint 118 has a set screw to connect to a linear translator mechanism including a rack 306, a pinion 310 and a carriage 308. Pinion 310 is used to adjust the height of positional adjuster 300 thereby allowing an operator to make precise and controlled adjustments to vertically position the surgical instrument. A second linking rod 314 extending from the rack 306 includes a second set screw 316. Set screw 316 is used to connect to a surgical instrument (not shown). Thus a surgeon can make angular adjustments utilizing the spherical joint 118 and linear translations utilizing adjustment platform 110 and finally fine tune the position of an attached surgical instrument using the rack and pinion linear translation of positional adjuster 300. Utility plate 104 may be configured as a shelving tray to hold and retain surgical instruments such as forceps, scissors, clamps, retractors, scalpels, etc. Modified utility plates may function as a surgical workstation in addition to facilitating ready access to surgical instruments during surgical procedures.

Figure 5:
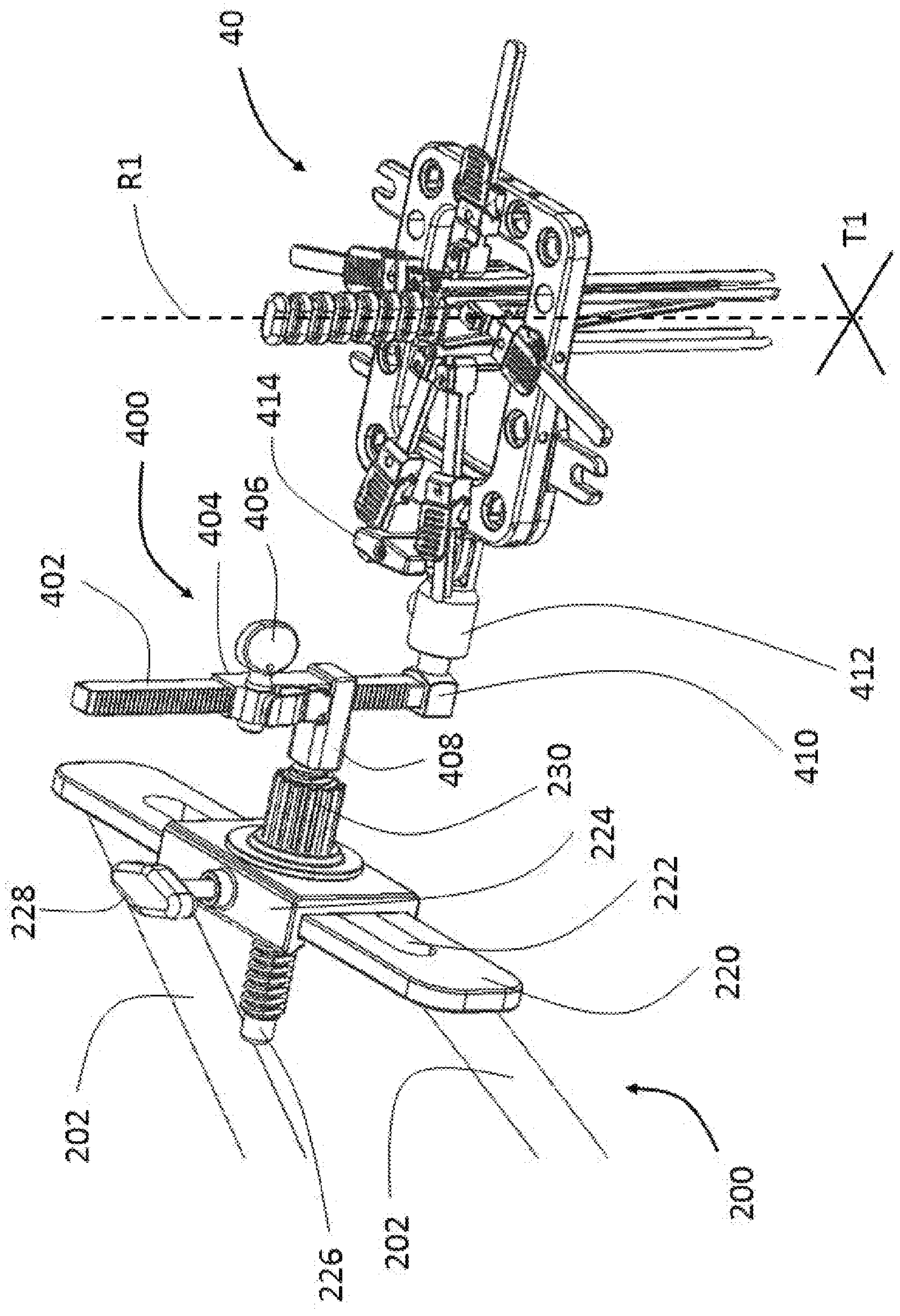
FIG. 5 is a perspective view of a positional adjuster attached to the rigid arm of FIG. 2 according to another embodiment of the present disclosure.

FIG. 5 shows adjustment platform 220 and attached positional adjuster 400 according to another embodiment of the present disclosure. Adjustment platform 220 is attached to central arm 205 of rigid arm 200 and has a slide block 224 disposed in a slot 222 which allows linear translation of the slide block with reference to rigid arm 200. A set screw 228 is used to secure slide block 224 in fixed position. A threaded screw 226 extends transversely through slot 222 and is threadingly engaged with the slot. Screw 226 has an adjustment knob 230 which can be rotated to linearly translate the screw with reference to rigid arm. Thus, adjustment platform 220 can be adjusted to linearly translate in a superior-inferior direction and a medial-lateral direction.

Positional adjuster 400 is attached to threaded screw 226 by a carriage 408. A rack 402 is disposed though the carriage and connects to lateral retractor assembly 40 through a spherical joint 412. A pinion 406 located on rack 402 allows for vertical adjustment of lateral retractor assembly 40. A linking rod 414 can be set in an unlocked mode to allow rotation of lateral retractor 40 via the spherical joint 412 with respect to positional adjuster 300. Once lateral retractor 40 is aligned as desired, the linking rod can be set to a locked mode to fix the position of the lateral retractor. Thus, a surgeon can make angular adjustments utilizing spherical joint 412 and linear translations utilizing adjustment platform 220 and positional adjuster 400 to fine tune lateral retractor assembly 40 position RI to a target surgical site T1. Other embodiments may include positional adjusters with spring loaded devices that will force the attached surgical instrument towards the surgical bed such that the surgical instrument is pressed against the target surgical site.

Figure 6B:
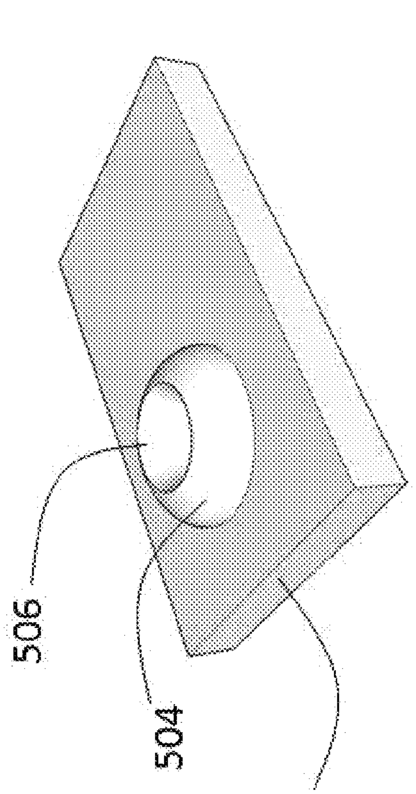
FIG. 6B is a perspective view of a first plate of the ball-adjuster of FIG. 6A.
Figure 6A:
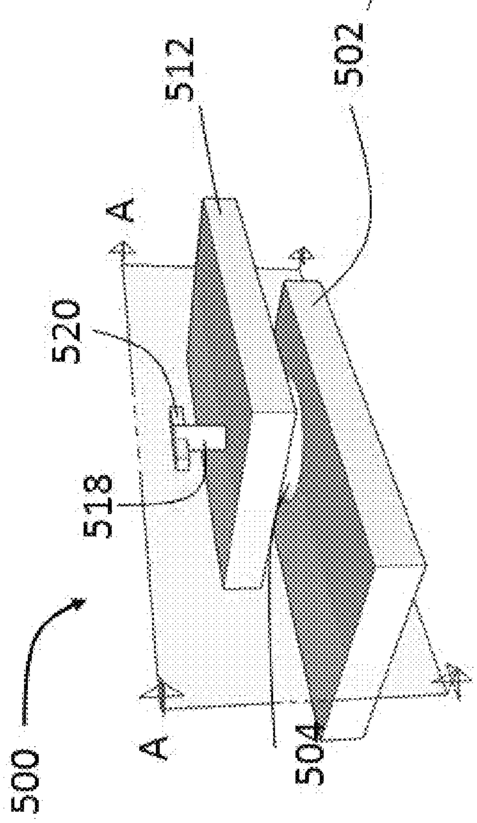
FIG. 6A is a perspective view of a ball-adjuster according to one embodiment of the present disclosure.

Referring now to FIG. 6A, there is shown a ball joint assembly 500 according to another aspect of the present disclosure. Ball joint assembly 500 can be attached as an interface between a rigid arm and a surgical instrument to support and position the surgical instrument. Ball joint assembly 500 includes a first plate 502 and a second plate 512. First plate 502 can be attached to the rigid arm and the surgical instrument can be attached to the second plate 512 (not shown). First plate 502 includes a hollow half-dome structure 504 as best shown in FIG. 6B. A recess 506 extends through the half-dome structure 504 and first plate 502.

Figure 6C:
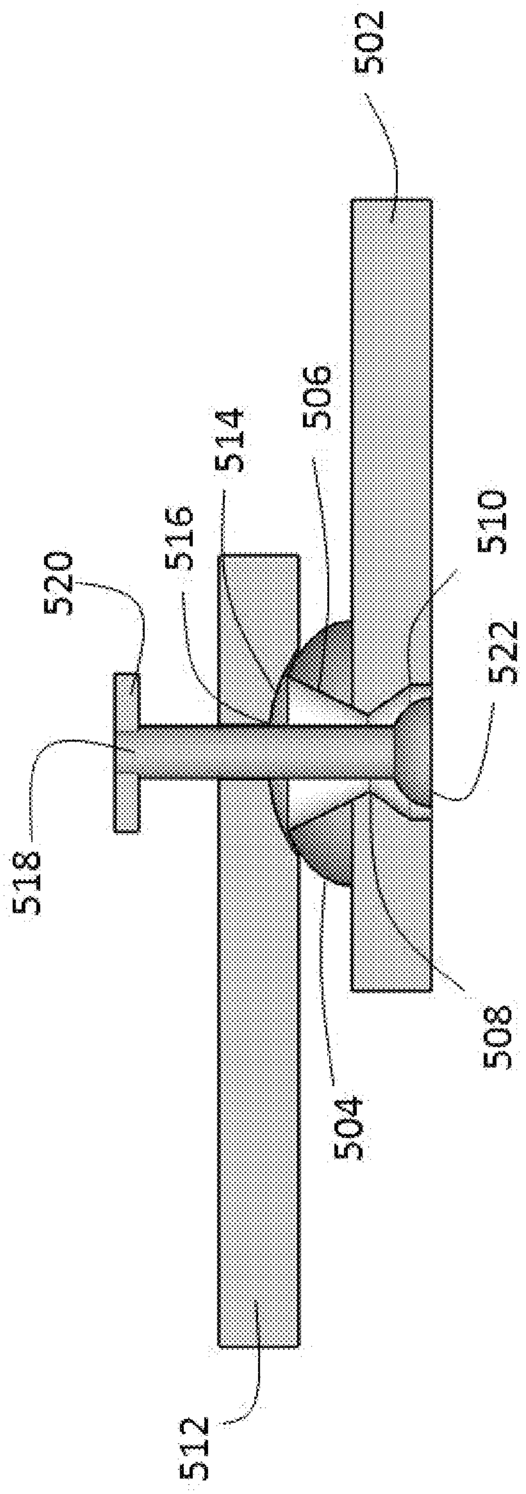
FIG. 6C is a cross-sectional view of the ball-adjuster of FIG. 6A.

FIG. 6C shows a cross-section view of ball joint assembly 500 along line A-A shown in FIG. 6A. Second plate 512 is provided with a half-dome receiver 514 that corresponds to and mates with half-dome structure 504. A threaded set screw 518 is positioned through recess such that it extends through the first plate 504 and second plate 512. Set screw 518 includes an enlarged head 522 which prevents pull out of the set screw on account of a pinch point 508 provided first plate 502. A handle 520 on an opposite end of set screw is used to force plate 512 on to plate 502. Thus, a surgeon can utilize ball joint assembly 500 to rotate and position a surgical instrument. Once the desired positon is achieved, a surgeon can then use the rotating handle 520 to lock the surgical instrument in position. This assembly can be utilized in lieu of the above discussed components for positioning a retractor assembly 40 or the like.

Figures 7A, 7B, 7C, 7D:
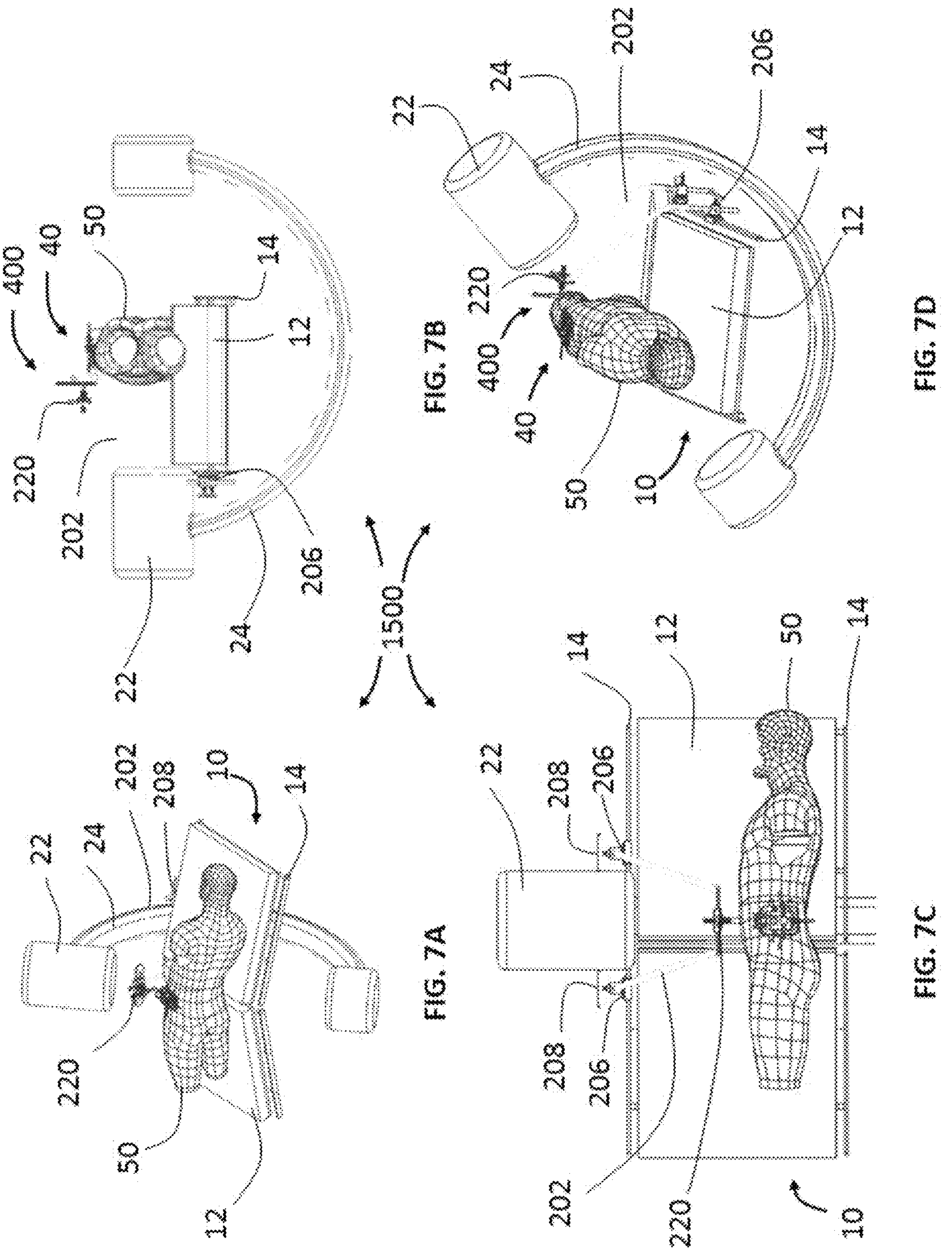
FIGS. 7A-D are perspective, top, and side views, respectively, of the rigid arm of FIG. 2 showing its relationship to a C-arm fluoroscopy system and patient.

Referring now to FIGS. 7A-7D, there is shown a surgical kit 1500 for performing lateral access spinal surgery along with C-arm x-ray assembly 20 in various positions according to another embodiment of the present disclosure. The surgical kit includes rigid arm 200, positional adjuster 400 and lateral retractor assembly 40. FIG. 7A shows lateral retractor assembly 40 positioned over the target surgical site. C-arm 20 is rotated to a first position wherein an x-ray device 22 is aligned in a lateral-medial direction with reference to patient 50 to obtain imaging in a first direction. As seen in FIG. 7A, clearance provided between the arms of rigid arms 200 allow for x-ray device to be readily positioned. FIGS. 7B and 7C shows C-arm 20 rotated and positioned to a second position wherein x-ray device 22 is aligned in an anterior-posterior direction with reference to patient 50 to obtain imaging in a second direction. The transition from the first position to the second position of the x-ray device 22 can be performed without disturbing surgical kit 1500. Similarly, a third set of imaging can be obtained in a third direction by positioning C-arm 20 as shown in FIG. 7D without displacing the surgical kit 1500 position. Thus, surgical kit 1500 allows for the C-arm to be positioned in multiple directions without disturbing the surgical kit 1500 to obtain images as necessary. Consequently surgical kit 1500 may reduce considerable time and effort in procedures requiring multiple C-arm imaging from different directions.

Figure 8A:
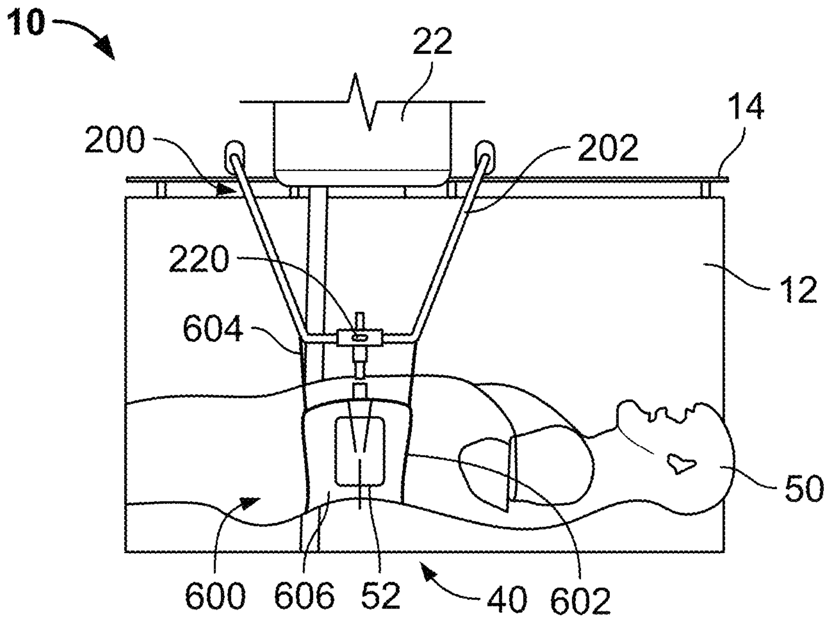
FIG. 8A is a top view of a frame relative to a patient according to one embodiment of the present disclosure.
Figure 8B:
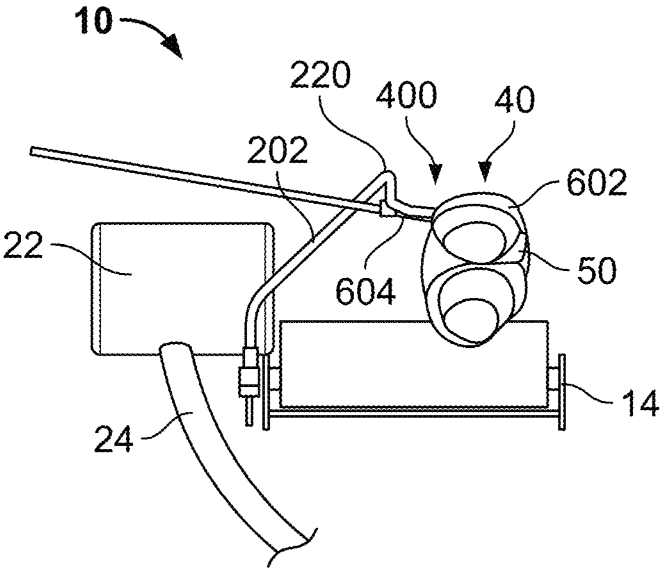
FIG. 8B is a side view of the frame of FIG. 8A.

Referring now to FIGS. 8A and 8B, there is shown a frame 600 according to another embodiment of the present disclosure. Frame 600 includes a saddle-shaped harness 602. Harness 602 is mounted on a target surgical site 52, which, in the particular embodiment shown, is located on a lateral side of patient 50. As best shown in FIG. 8B, harness 602 extends from an anterior to a posterior side of patient 50 and has a body-shaped contour enabling harness 602 to completely cover a lateral side of the patient including the target surgical site. A central window 606 allows a lateral retractor assembly 40 access to target surgical site 52. Attachment features 604 are used to secure harness 602 to rigid arm 200. The attachment features can be rigid or elastic to ensure that harness 602 is firmly secured on the target surgical site. When harness 602 is secured on patient 50, the weight and body-shaped contour of harness 602 will confine patient 50 to surgical bed 10. Alternatively, a biasing element, such as a spring loaded device, can be used to further force harness 602 on patient 50 and thereby firmly secure the patient to the surgical bed to minimize displacement between the patient and the surgical instruments.

Figure 9A:
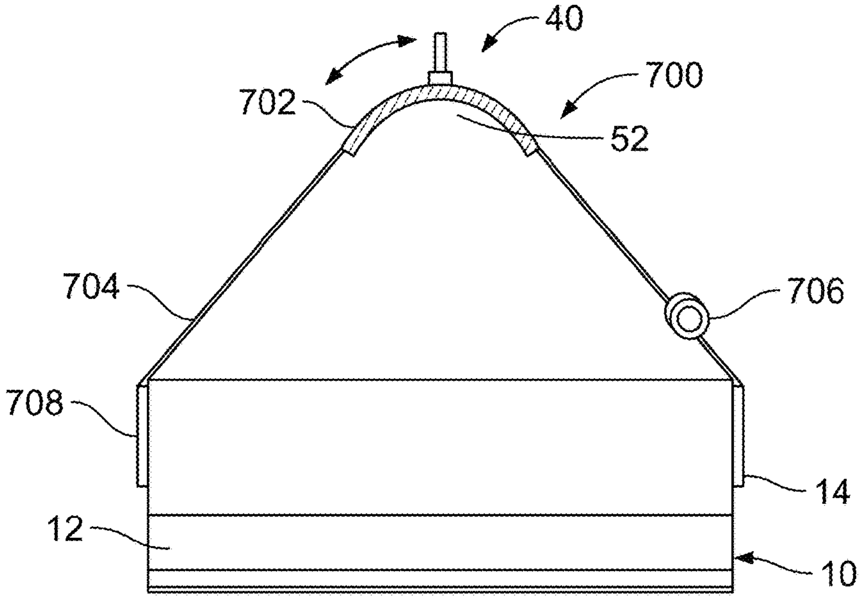
FIG. 9A is a side view of a frame according to another embodiment of the present disclosure.
Figure 9B:
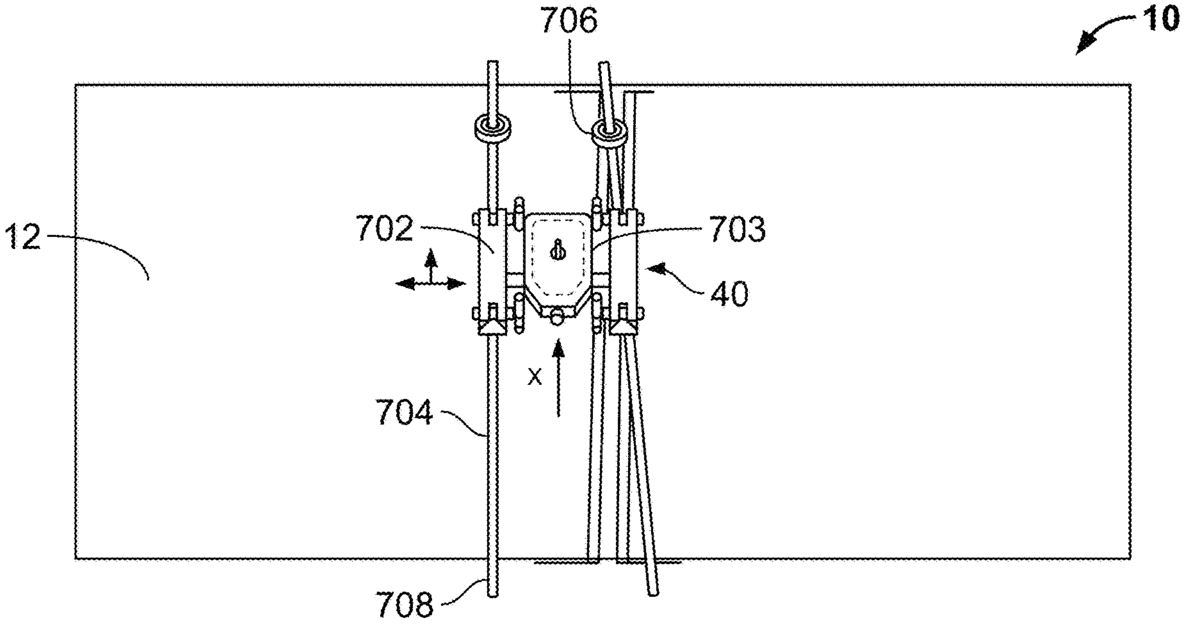
FIG. 9B is a top view of the frame of FIG. 9A.

FIGS. 9A and 9B show a frame 700 according to another embodiment of the present disclosure. Frame 700 includes a saddle-shaped harness 702 secured to surgical bed 10 by attachment members 704. Attachment member 704 can be rigid or elastic to securely position harness 702 on a target surgical site on patient 50. One end of each attachment member is connected to harness 702 and the opposite end is connected to straps 708 on surgical bed 10. As best show in FIG. 9A, harness 702 extends from an anterior to a posterior side of patient 50 and has a body-shaped contour enabling harness 702 to completely cover a lateral side of the patient including a target surgical site 52. A central window 703 allows a lateral retractor assembly 40 access to target surgical site 52. Attachment members 704 include tensioners 706 to control the pressure exerted by harness 702 on patient 50. For example, tensioners 706 can be adjusted to increase tension in attachment members 704 and force harness 702 on to patient 50 thereby enabling frame 700 to secure patient to surgical bed 10. As best shown in FIG. 9B, four attachment members 704 form a track to allow harness 702 to be positioned along the length of the track. Although four attachment members are shown in this embodiment, other embodiments may more or less attachment members.

Figure 10A:
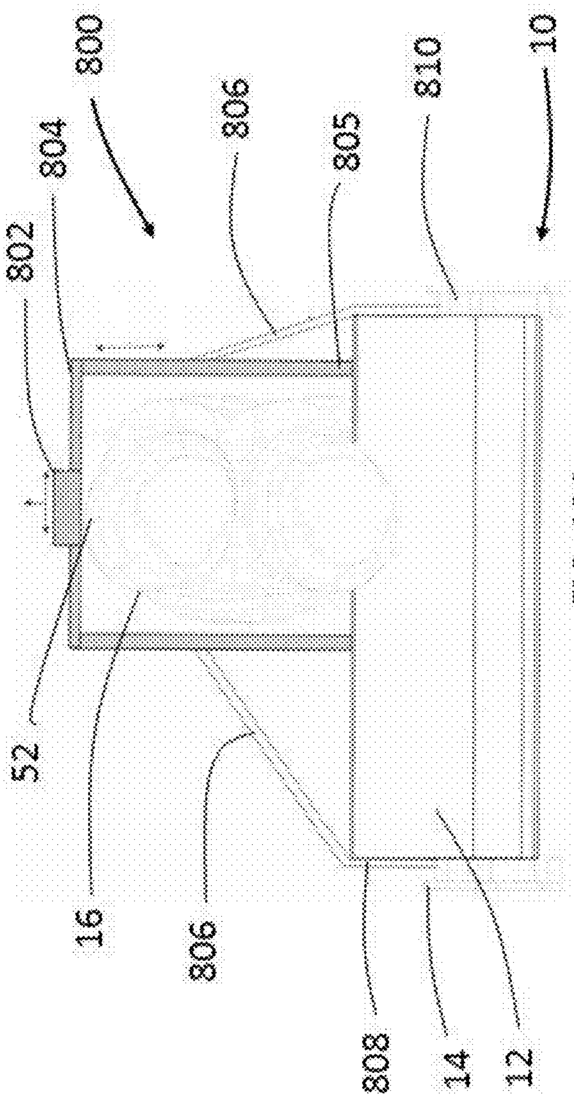
FIG. 10A is a side view of a frame relative to a patient according to another embodiment of the present disclosure.
Figure 10B:
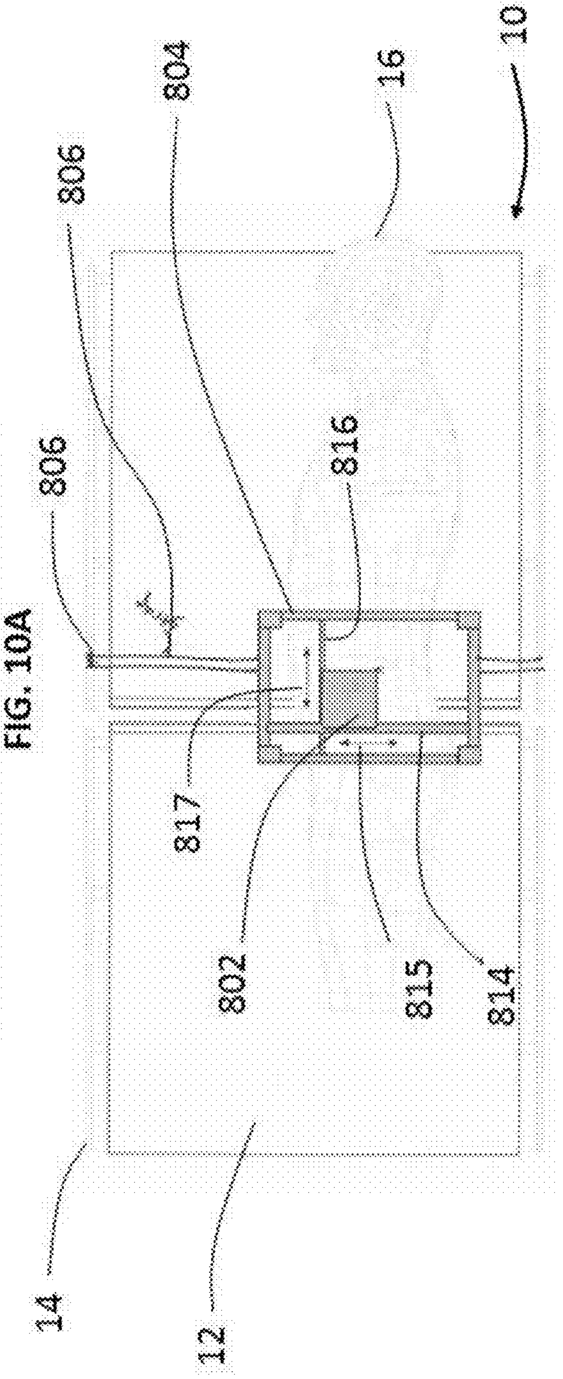
FIG. 10B is atop view of the frame of FIG. 10A.

Referring now to FIGS. 10A and 10B, there is shown a frame 800 according to another embodiment of the present disclosure. Frame 800 includes a rectangular platform 804 with legs 805 extending towards surgical bed 10 to support frame 800. Frame 800 is placed over patient 50 such that the rectangular platform 800 is located over target surgical site 52. Legs 805 of frame 800 confine and hold patient 50 on surgical bed 10 as best shown in FIG. 10A. Rectangular platform 50 includes a moving plate 802 that translates in a first direction 815 along element 814 and a second transverse direction 817 along element 816 as best shown in FIG. 10B. Elements 814 and 816 allow moving plate 802 to translate and be locked to a fixed position within rectangular platform 804. Thus a surgical instrument (not shown) attached to moving plate 802 can be readily positioned over surgical site 52. One or more attachment members 806 are used to secure frame 800 to surgical bed 10.

Figure 11:
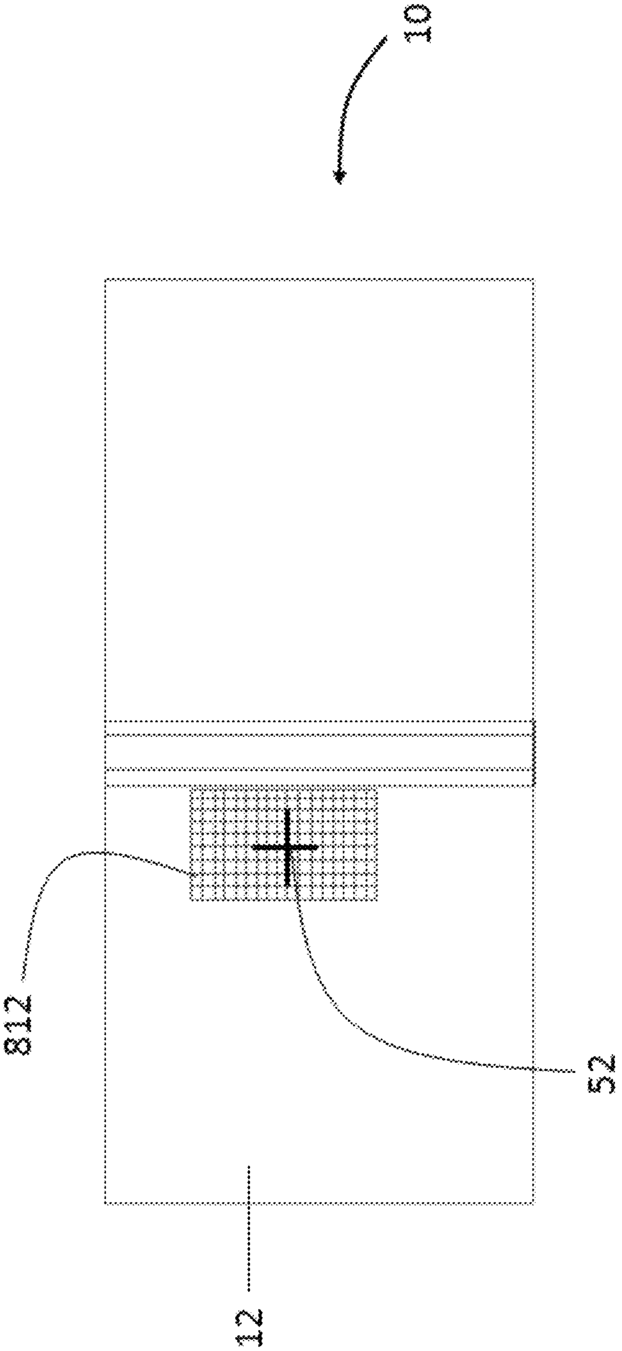
FIG. 11 is a top view of a positioning grid according to one embodiment of the present disclosure.

FIG. 11 shows a positioning grid 812 according to another embodiment of the present disclosure. Positioning grid 812 can be used in guiding linear translation of a surgical instrument in two directions for proper positioning of the surgical instrument. For example, in a spinal lateral access surgery procedure using frame 800, a lateral retractor attached to moving plate 802 can be precisely positioned over target surgical site 52 using the positioning grid as reference. Positioning grid 812 can be used in conjunction with x-ray system 20 to facilitate proper positioning of surgical equipment. Additionally, positioning grid 812 may be pre-operatively configured to be patient-specific to further enhance precision of surgical equipment positioning during surgery. Positional grid 812 may consist of a metal mesh configured to appear as a grid on an x ray or other visualization systems to aid a surgeon in determining the target surgical site. Positional grid 812 may also be made of non-metallic compositions and may consist of any material sufficient to produce an x-ray signature or other visualization signature depending on the selected visualization system.

Figure 12A:
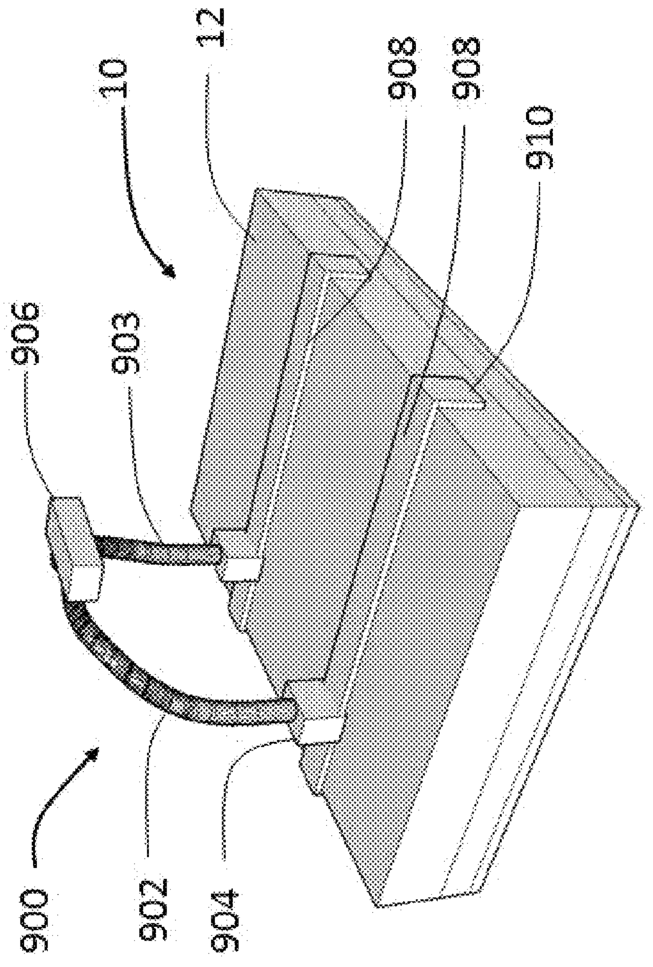
FIGS. 12A and 12B are perspective and top views, respectively, of a rigid arm according to another embodiment of the present disclosure.
Figure 12B:
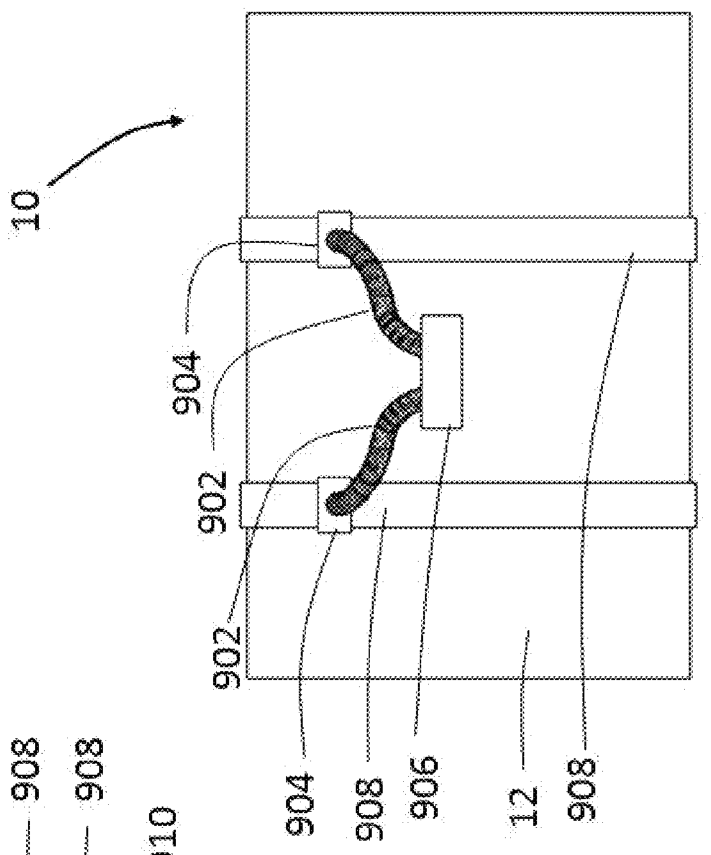

Referring now to FIGS. 12A and 12B, there is shown rigid arm 900 according to another embodiment of the present disclosure. Rigid arm 900 includes a first arm 902 and a second arm 903 connected to an accessory block 906. Arms 902 and 903 are attached to strap connections 910 located on surgical bed 10. Sliding blocks 904 are used to secure arms 902 and 903 to surgical straps 910. Arms 902 and 903 extend vertically and horizontally above surgical bed 10 as best shown in FIG. 12A. Accessory block 906 is generally horizontal to surgical bed 10 and located over interior bed surface 12. Accessory block includes attachment mechanisms as more fully described above to connect surgical instruments. Sliding blocks 904 allow arms 902, 903 to be moved and fixed into any desired positioned along strap connections 906. All components of rigid arm 900 are located on one side of surgical bed 10 and therefore provide unrestricted access to a surgeon located on an opposite or transverse side of the surgical bed.

Figure 13A:
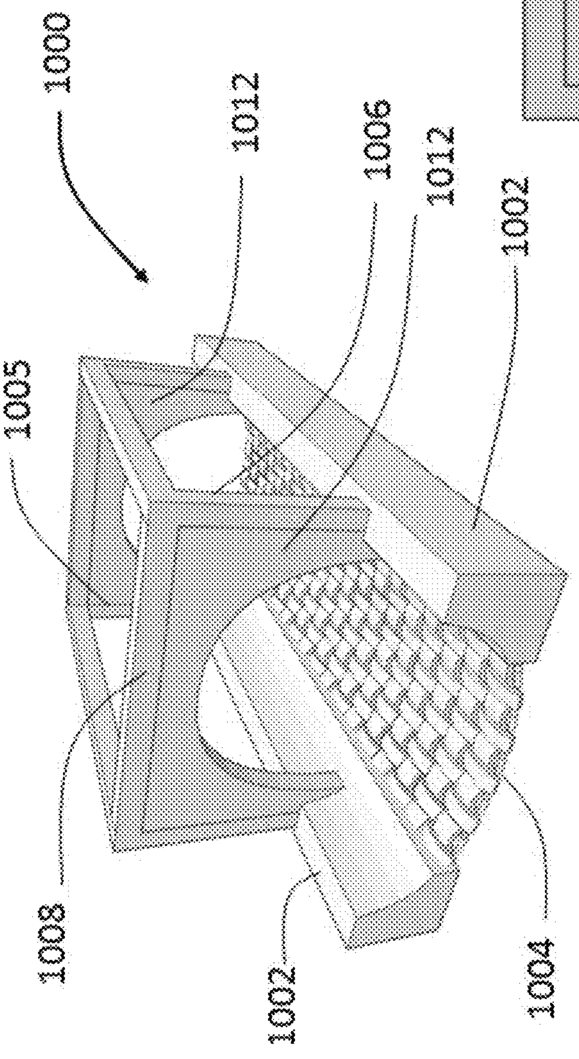
FIG. 13A is a perspective view of a bed with a frame according to one embodiment of the present disclosure.
Figure 13B:
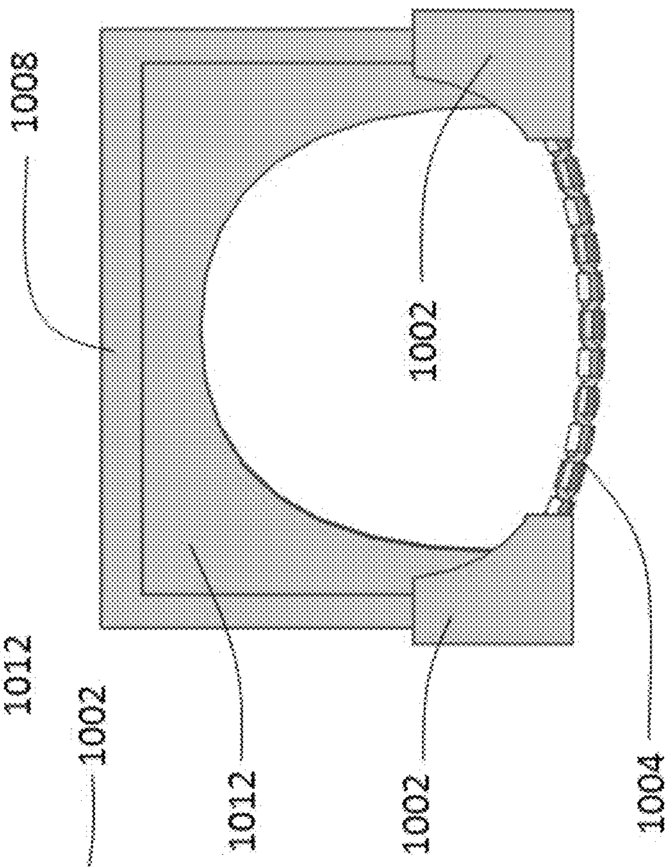
FIG. 13B is a side view of the bed and the frame of FIG. 13A.

FIGS. 13A and 13B show a surgical bed frame 1000 according to one embodiment of the present disclosure. Bed frame 1000 includes a frame 1008, sling barriers 1002, and a flexible bed surface 1004. Frame 1008 includes an open rectangular window 1005 to allow access to a patient (not shown) positioned on flexible bed surface 1004. Frame 1008 includes securing inserts 1012 contoured to wrap around a patient's body and hold the patient to flexible bed surface 1004. Securing inserts 1012 may be detachable such that a surgeon may first place frame 1008 over a patient and then position securing inserts 1012 to restrain the patient. Sling barrier 1002 located on either side of surgical bed flexible bed surface 1004 provide additional support to hold and retain patient in the desired position. Flexible bed surface 1004 is configured to support and generally flex to a concave profile to securely hold and retain a patient.

Figure 14A:
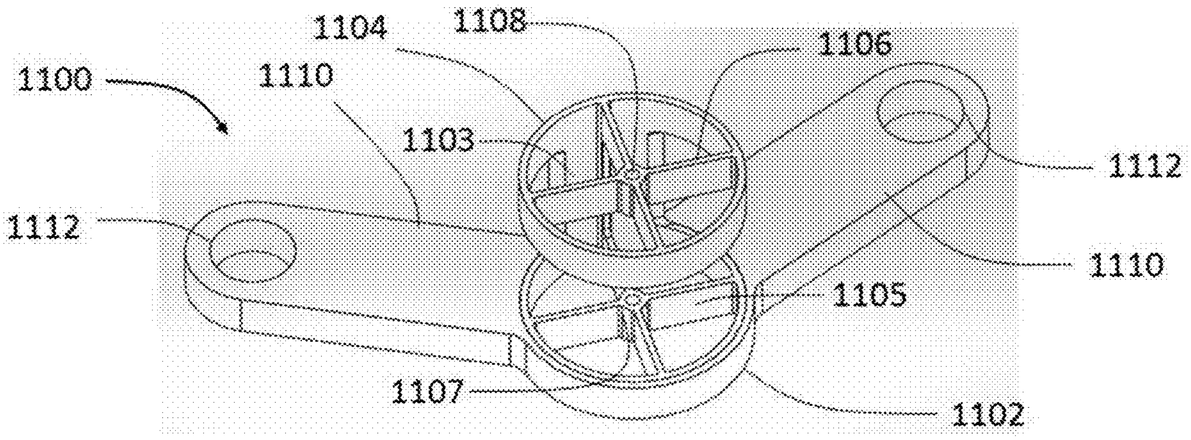
FIG. 14A is a perspective view of an alignment guide according to one embodiment of the present disclosure.
Figure 14B:
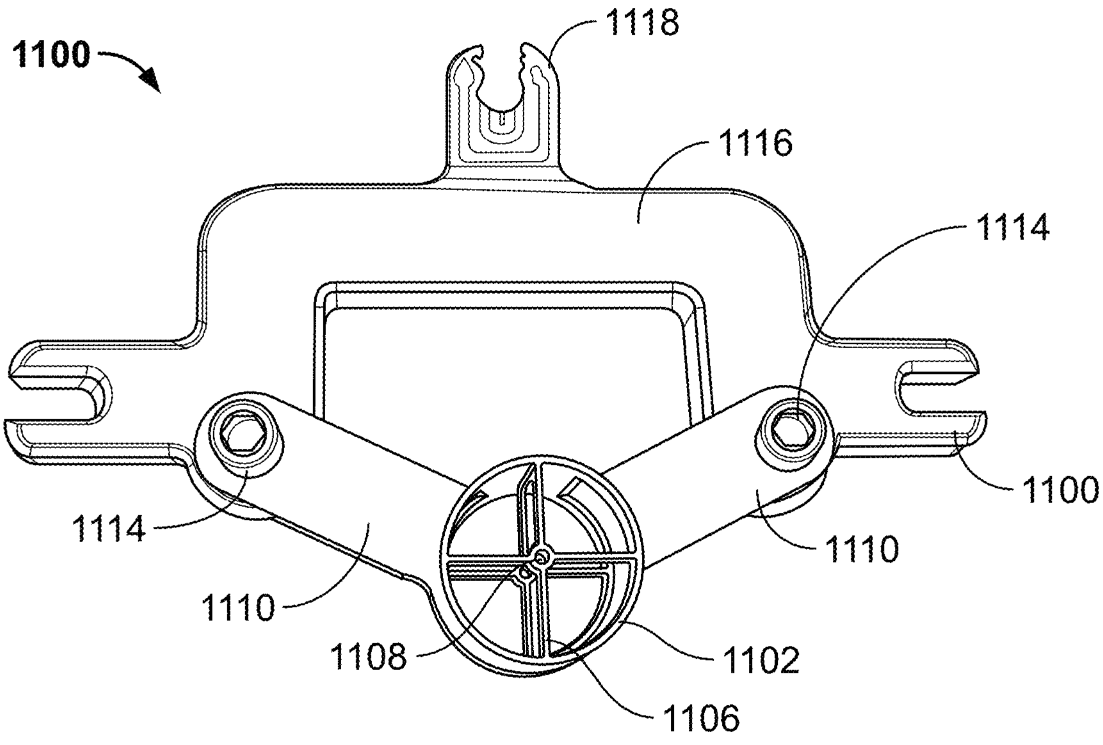
FIG. 14B is a top view of the alignment guide of FIG. 14A secured to an adapter.

Another concept of the present disclosure is a targeter assembly which can be used to align the rigid arm assembly at the desired target surgical site and can be utilized with any of the foregoing embodiments. FIG. 14A shows a targeter assembly 1100, which includes a bottom frame 1102 and a top frame 1104, separated over a distance by a spacer 1103. Both bottom frame 1102 and top frame 1104 are shown as having round profiles, however, the present disclosure contemplates square, triangular, rectangular, or any other multi-sided geometric configuration for the profile of the frames. Frames 1102, 1104 have an internal void through which can be viewed objects beyond the geometry of the frames. Within the void of bottom frame 1102 is at least one bottom cross-bar 1105. While four cross-bars are shown in FIG. 14A, other embodiments may have different number of cross-bars. Attached to bottom cross-bar 1105 is a bottom central target 1107, which is depicted as round but may take any geometry, such as square, triangular, rectangular, or any other multi-sided geometric configuration. The bottom central target may possess a void in the center of its geometry as shown in FIG. 14A, but it also may be solid throughout. Attached to one side of bottom frame 1102 is spacer 1103, which extends parallel to an inwards oriented face of the bottom frame 1102 and extends an undefined length until it attaches to top frame 1104, such that the spacer 1103 extends parallel to an inwards oriented face of top frame 1104. Similar to bottom frame 1102, within the void of top frame 1104 is at least one top cross-bar 1106 which is attached to the inwards oriented face of top frame 1104. Attached to top cross-bar 1106 is a top central target 1108. Top central target 1108 may possess a void in the center of its geometry, such as shown in FIG. 14A, but it also may be solid throughout. The geometries described above are such that when viewed from the top down, all elements align to create a unified image, such as is shown in FIG. 14B.

Attached to the outwards oriented face of the bottom frame 1102 is at least one arm 1110. FIGS. 14A-B depict two arms 1110 extending out of bottom frame 1102, each arm having an aperture 1112 at the end furthest from the bottom frame 1102. While FIG. 14A-B both depict the arms 1110 extending from the bottom frame, the present disclosure contemplates the arms emanating from top frame 1104, or from both the bottom frame 1102 and top frame 1104. Apertures 1112 are used with fasteners 1114 to secure the aforementioned elements to a block 1116 (see FIG. 14B) having a connector 1118. The block 1116 is depicted as having a c-shape, but it may possess any geometry that is capable of receiving arms 1110 and securing through aperture 1112 and fastener 1114.

Figure 14C:
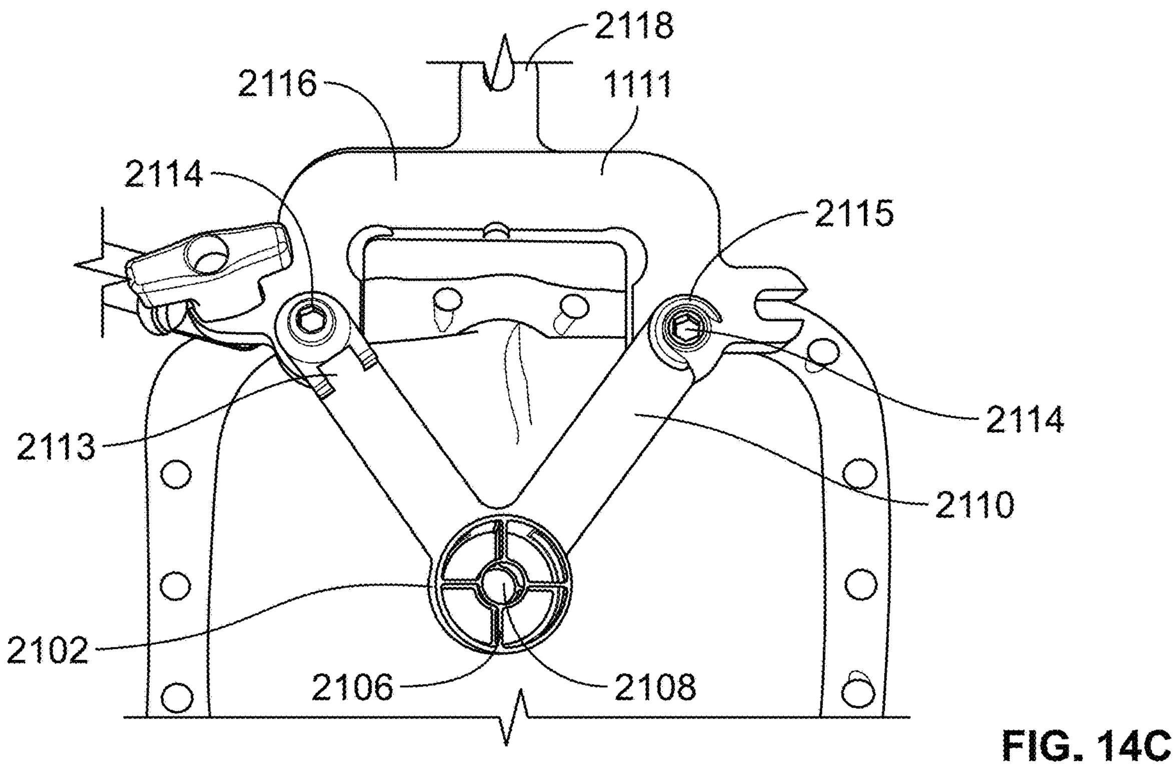
FIGS. 14C-D are top and perspective views of an alignment guide according to another embodiment of the present disclosure.
Figure 14D:
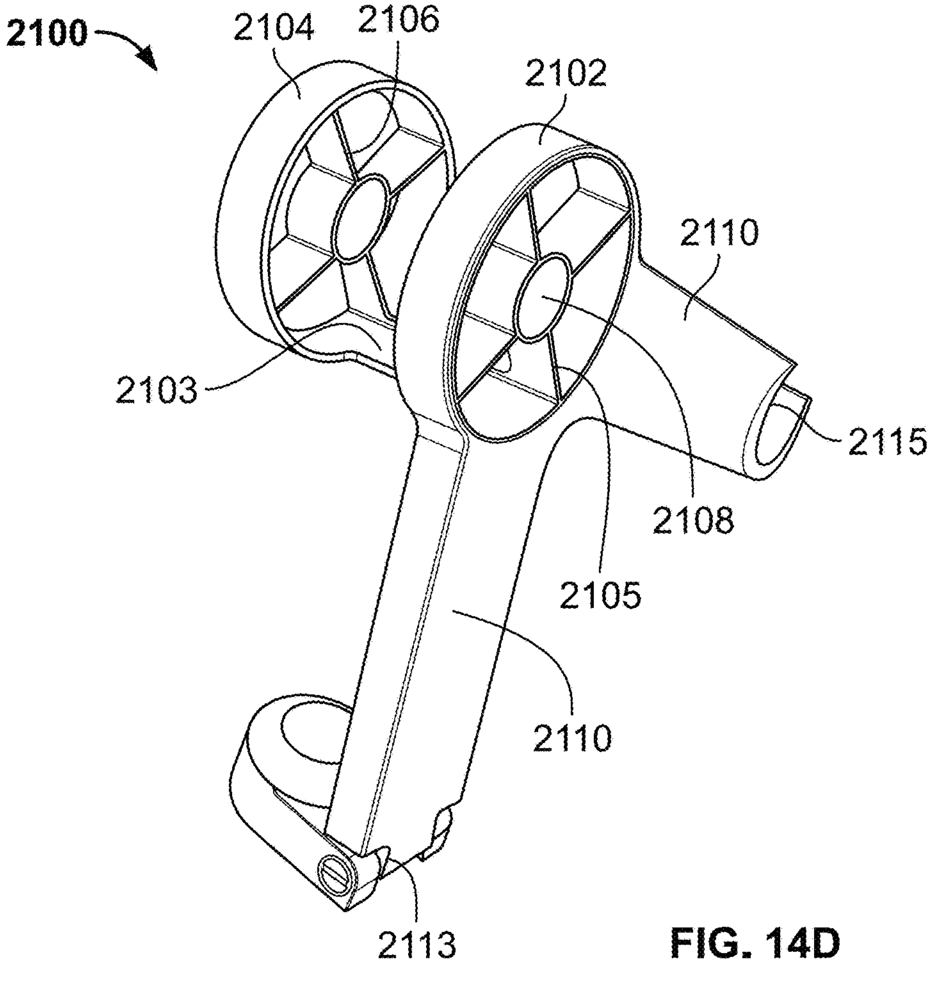

FIG. 14C show a targeter assembly 2100 according to another embodiment of the present disclosure. Targeter assembly 2100 is similar to targeter assembly 1100, and therefore like elements are referred to with similar numerals within the 2100-series of numbers. For instance, targeter assembly 2100 includes a bottom frame 2102 and a top frame 2104, separated over a distance by a spacer 2103. However, targeter assembly 2100 includes a hinge 2113 at one arm 2110 as shown in FIG. 14C. In this embodiment, the targeter assembly 2100 is capable of disengaging from a fastener 2114 by means of a semi-circular slot 2115 and rotating about hinge 2113 in order to clear the working space of the targeter assembly 2100 as best shown in FIG. 14D. While a hinge is shown in this embodiment, other embodiments may have a ball and socket joint or other similar features to allow the targeter assembly to be positioned as described herein. Hinges or other similar features may be provided on both arms. Targeter assembly 2100 can be subsequently moved back into its original position with disengaged fastener 2114 by once again engaging and securing the corresponding arm 2110.

Figure 15A:
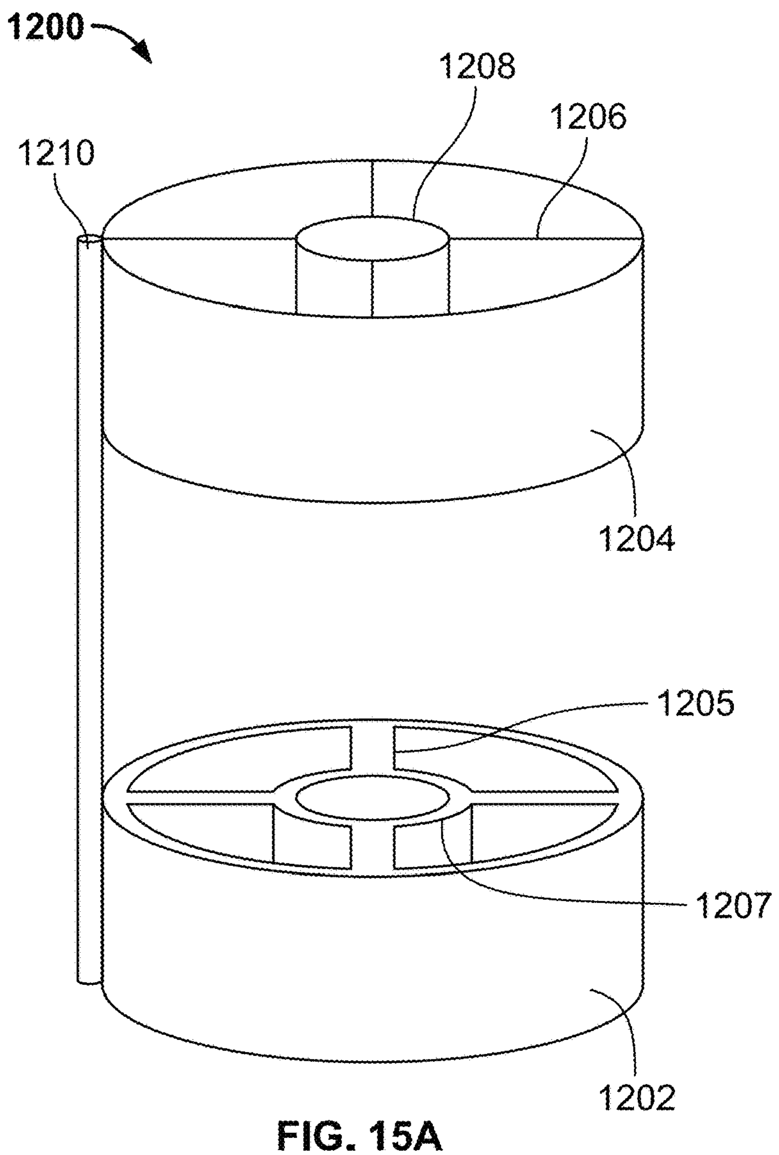
FIGS. 15A-B are partial side and top views of an alignment guide according to another embodiment of the present disclosure.
Figure 15B:
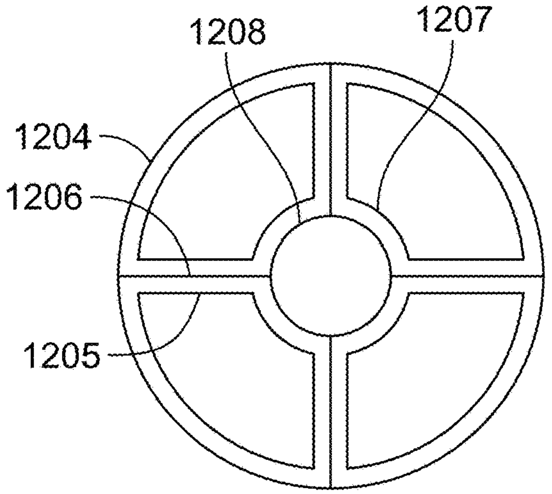

FIGS. 15A and 15B show a targeter assembly 1200 according to another embodiment of the present disclosure. Targeter assembly 1200 includes a bottom frame 1202, a spacer 1210, a top frame 1204, top cross bars 1206, and a top central target similar to targeter assembly 1100 shown in FIGS. 14A-B and described above. However, the elements within the void of bottom frame 1202 are different. Notably, at least one bottom cross-bar 1205 include a double-wall design which involve two similar structures separated by a vacancy, where a user could view through the vacancy and observe an object beyond the geometry of the bottom cross-bars 1205. The same can be said about bottom central target 1207, which is connected the bottom cross-bars 1205 and also incorporates a double-wall design. When viewed from above, an observer will see top cross-bars 1206 as 'framed' or outlined by the profiles of the double-walls of bottom cross-bars 1205. Similarly, the observer will see top central target 1208 as 'framed' or outlined by the profile of the double-walls of bottom central target 1207. This design further captures the utility of the present disclosure by providing further visual feedback about the alignment of the targeted assembly, allowing for faster adjustment and optimization of the alignment.

Figure 16A:
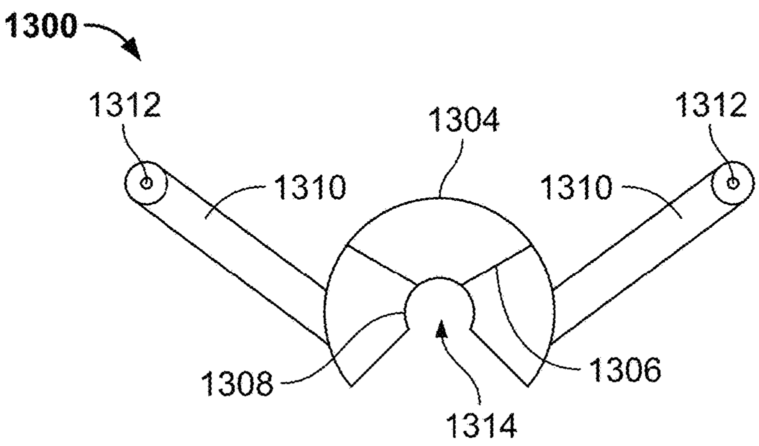
FIGS. 16A-D are top and side views of an alignment guide according to another embodiment of the present disclosure.
Figure 16B:
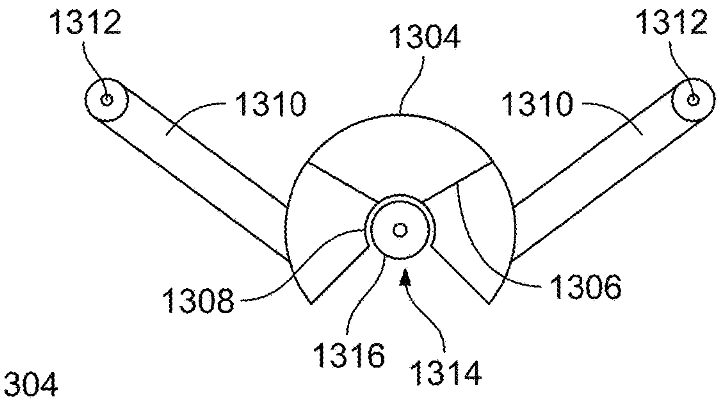
Figure 16C:
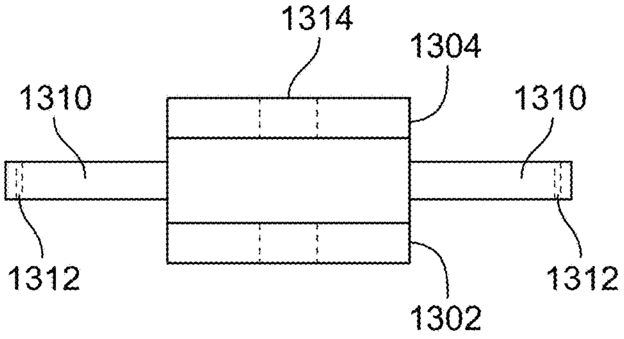
Figure 16D:
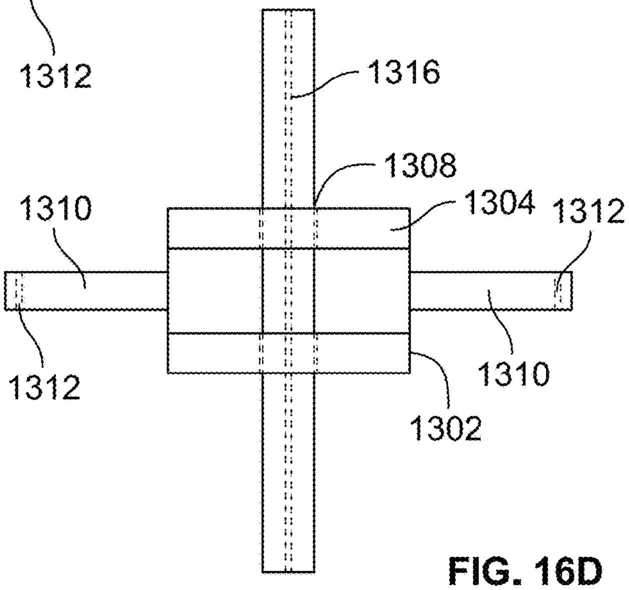

A targeter assembly 1300 shown in FIGS. 16A-D is similar to targeter assembly 1100. Targeter assembly 1300 includes a bottom frame 1302 and atop frame 1304, separated over a distance by a spacer 1103. Both the bottom frame 1302 and top frame 1304 are shown as having crescent profiles, however, the present disclosure contemplates square, triangular, rectangular, or any other multi-sided geometric configuration for the profile of the frames that has at least one open side. The frames 1302, 1304 have an internal void through which can be viewed objects beyond the geometry of the frame. Within the void of bottom frame 1302 is at least one bottom cross-bar 1305 which is attached to the inwards oriented face of bottom frame 1302. FIG. 16A depicts four cross-bars, but any number may be sufficient to achieve the utility of the present disclosure. Within the void of top frame 1304 is at least one top cross-bar 1306 which is attached to the inwards oriented face of the top frame 1304. FIG. 16A depicts four cross-bars, but any number may be sufficient to achieve the utility of the present disclosure. Top cross-bars 1304 meet to form an aperture 1312, and similarly the bottom cross-bars 1302 meet to form an aperture 1312. This aperture is accessible through at least the open side of the crescent shape of bottom frame and top frame 1302, 1304. Within aperture 1314, a guidewire 1316 can be inserted, either from the top or from the open side.

A laser or other light projections means can be inserted into aperture 1314 to project a marker on the incision site. The laser can be inserted from either the top or from the open side and positioned to precisely mark the incision site. The laser may be used to project the laser marker on the target site once the targeter assembly 1300 has been properly aligned over the surgical site.

Figure 17A:
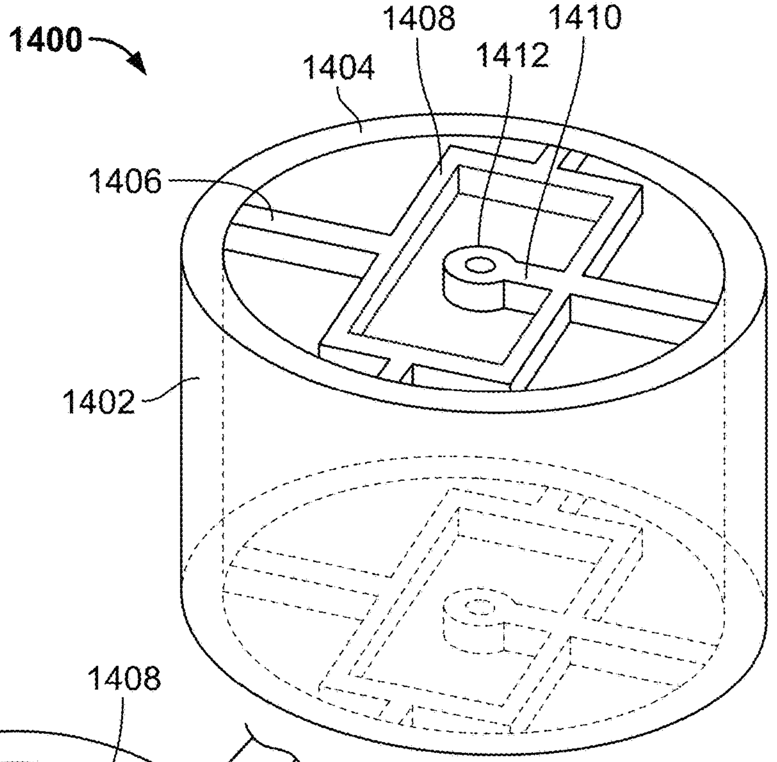
FIGS. 17A-C are perspective and top views of an alignment guide according to another embodiment of the present disclosure.
Figure 17B:
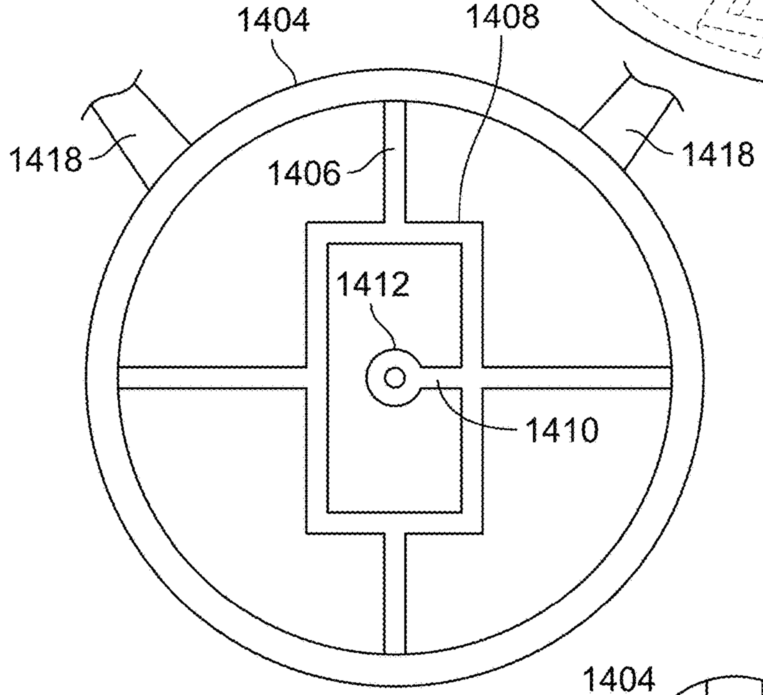
Figure 17C:
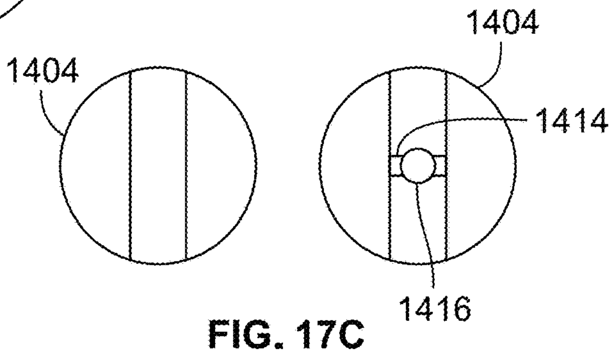

FIGS. 17A-C show a targeter assembly 1400 according to another embodiment of the present disclosure. Targeter assembly 1400 includes a cylinder 1402, cross-bars 1406, and a central targeter 1212. Cylinder 1402 serves a similar purpose as spacer 1103 of targeter assembly 1100, but instead cylinder 1402 has a completed circular geometry. A cylinder face 1404 subsequently serves the same utility purposes as top frame 1104 of targeter assembly 1100. Attached to the top of the internal face of cylinder 1402 are cross-bars 1406, which extend towards the center of cylinder 1402 until they meet a rectangular frame 1408. Rectangular frame 1408 has an inwards facing surface, to which at least one central targeter arm 1410 is attached. The opposite portion of central targeter arm 1410 is attached to a central targeter, which is located at the center point of the geometry of the cylinder face 1404. Similar elements are attached to the bottom of the internal face of the cylinder 1402, aligned so that when viewed from the top, only one grouping of elements would be visible, as shown in FIG. 17B. FIG. 17C shows yet another possible assembly of the targeter assembly 1400, wherein a more narrow viewing portal is bridged by at least one central targeter arm 1414 which is subsequently attached to a central targeter 1412, the central targeter 1412 being located at the center point of the geometry of cylinder face 1404.

The aforementioned targeter assemblies operate in a similar manner and the utilization of these assemblies are as described above with reference to FIGS. 14A-B and FIGS. 16A-D. The targeter assembly 1100 of FIGS. 14A-B, for example, are attached to a rigid arm 100 at utility plate 104 through connector 1118. Alternatively, targeter assembly 1100 can be attached to a positional adjuster 300, which subsequently connects to utility plate 104 of rigid arm assembly 100. The user uses the rigid frame assembly to locate the target assembly 1100 above a possible incision point on patient 50. The user then locks the assembly into place and swings C-arm xray 22 into alignment with the targeter assembly 1110, such that C-arm xray is aligned with the view in FIG. 14B. The user then takes an x-ray and examines the image. If the user can see only the elements attached to top frame 1104, then the user knows that assembly is aligned correctly and that an incision at that point will reach the structures that appear on the x-ray that can be viewed through the voids in the targeter assembly 1100. If the user can view the elements attached to both the bottom and top frames, then the user known the assembly is not aligned correctly and that the user must readjust the rigid arm assembly and repeat the process until the assembly is properly aligned. Once properly aligned, the user returns the C-arm xray to its original position and exchanges the targeter assembly 1100 for a retractor assembly and completes the procedure.

The assembly depicted in FIGS. 16A-D incorporates the ability to laterally install a guidewire which allows for a more accurate assessment of the alignment of the targeting assembly. In this configuration, once the user has properly aligned the targeter assembly, a guidewire can be inserted into the assembly and pushed into a surgical incision until it rests against a vertebral body of the patient. Once the user has assured proper alignment of the probe against the vertebral bodies, the user can remove the targeter assembly while leaving the guidewire in place, using the guidewire as a guide for assisting in the alignment of the retractor assembly in furtherance of the rest of the procedure replacing or repairing a vertebral disc. While all other embodiments consider the use of such a guidewire, the assembly depicted in FIGS. 16A-D simplifies utilization of the guidewire given the restrictions inherent in the workspace.

While a surgical instrument such as retractor for a lateral spinal surgery procedure is described in conjunction with these embodiments, other surgical instruments for use in other surgical procedures may also use the embodiments described herein. For instance, the rigid arms, frames and targeter assemblies disclosed herein can be utilized in anterior, posterior spinal surgery or the like. The surgical instruments disclosed herein may be made with polymers such as PEEK, carbon fiber reinforced PEEK, PAEK, UHMWPE, metals, ceramics, combinations of the foregoing, or other suitable materials that possess sufficient strength and rigidity. Additive manufacturing techniques such as 3D printing may be used to fabricate surgical instruments of the present disclosure.

Independent Rod Suspension

The structures, systems and methods as described herein may be used to expand rods of a retractor where at least one rod varies in shape in response to changes in loading on the rod. Details of such rods forming part of a retractor assembly are described in the '841 Application.

Lateral Access Bridges, Shims and Lighting Including Rod Lighting

The structures, systems and methods as described herein may be part of a surgical procedure where after the surgical portal is fully expanded, bridges designed to maintain the portal size and shape and to provide light to the portal may be inserted to improve and enhance the surgical procedure, such as those described in the '796 and '579 Applications. Rods, shims and other retractor components may also be used as described in the '579 Application.

Expanders for Rod Retraction

The structures, systems and methods as described herein may be part of a surgical procedure where at least some of the steps involved in distracting rods of a retractor involve the insertion of expanders in between the rods as described in the '847 Application, thereby increasing a surgical portal size in between such rods.

Furthermore, although the disclosure herein has been described with reference to particular features, it is to be understood that these features are merely illustrative of the principles and applications of the present disclosure. It is therefore to be understood that numerous modifications, including changes in the sizes of the various features described herein, may be made to the illustrative embodiments and that other arrangements may be devised without departing from the spirit and scope of the present disclosure. In this regard, the present disclosure encompasses numerous additional features in addition to those specific features set forth in the paragraphs below. Moreover, the foregoing disclosure should be taken by way of illustration rather than by way of limitation as the present disclosure is defined in the examples of the numbered paragraphs, which describe features in accordance with various embodiments of the disclosure, set forth in the claims below.

The invention claimed is:

1. A positional adjuster for a surgical instrument comprising:

an adjustable first linear rack and pinion actuator including a first handle for manipulation to position a surgical instrument in a proximal-distal direction, an adjustable second linear linking rod actuator including a second handle for manipulation to position the surgical instrument in an anterior-posterior direction, and an adjustable third linear linking rod actuator including a third handle for manipulation to position the surgical instrument in a medial-lateral direction, an adjustable spherical bearing joint to allow rotation of the surgical instrument in at least a first and a second plane so as to provide for angular rotation in two planes, a first section for detachable attachment to a body, and a second section for detachable attachment to the surgical instrument.

2. The positional adjuster of claim 1, wherein the first, second and third linear actuators are at least one of a electro-mechanical and a hydraulic actuator.

3. The positional adjuster of claim 1, wherein the second and third linear actuators are rack and pinion actuators.

4. The positional adjuster of claim 1, wherein the adjustable bearing joint is a gimbal.

5. The positional adjuster of claim 1, further including a second adjustable bearing joint to allow rotation of the surgical instrument in at least a third plane.

6. The positional adjuster of claim 1, wherein the first, second and third linear adjusters and the spherical bearing joint include locking screws such that the surgical instrument can be locked in a fixed position.

7. The positional adjuster of claim 1, wherein the surgical instrument is a retractor.

8. The positional adjuster of claim 1, wherein the body is a rigid arm.

* * * * *